US009481715B2

(12) United States Patent
Vernet et al.

(10) Patent No.: US 9,481,715 B2
(45) Date of Patent: Nov. 1, 2016

(54) PEPTIDES CAPABLE OF FORMING A CONVALENT COMPLEX, AND USES THEREOF

(75) Inventors: Thierry Vernet, Grenoble (FR); Anne-Marie Di Guilmi, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/007,024

(22) PCT Filed: Mar. 26, 2012

(86) PCT No.: PCT/EP2012/055333
§ 371 (c)(1),
(2), (4) Date: Oct. 18, 2013

(87) PCT Pub. No.: WO2012/127060
PCT Pub. Date: Sep. 27, 2012

(65) Prior Publication Data

US 2014/0030286 A1 Jan. 30, 2014

(30) Foreign Application Priority Data

Mar. 24, 2011 (FR) ..................................... 11 52432

(51) Int. Cl.

*A61K 39/09* (2006.01)
*A61K 39/085* (2006.01)
*A61K 39/00* (2006.01)
*C07K 14/315* (2006.01)

(52) U.S. Cl.

CPC .......... *C07K 14/3156* (2013.01); *A61K 39/09* (2013.01); *C07K 14/315* (2013.01); *G01N 2333/315* (2013.01)

(58) Field of Classification Search

CPC ....... A61K 39/00; A61K 39/02; A61K 39/09
USPC ......... 424/178.1, 184.1, 185.1, 192.1, 193.1, 424/234.1, 237.1
See application file for complete search history.

(56) References Cited

U.S. PATENT DOCUMENTS

2008/0260768 A1* 10/2008 Gilbert et al. ............. 424/190.1

FOREIGN PATENT DOCUMENTS

WO 2011098772 A1 8/2011

OTHER PUBLICATIONS

Brohawn, S., et al., "Crystal Structure of the Human K2P TRAAK, a Lipid- and Mechano-Sensitive K+ Ion , Channel", "Science", Jan. 27, 2012, pp. 436-441, vol. 335.
Budzik, J., et al . "Amide Bonds Assemble Pill on the Surface of Bacilli" "PNAS", Jul. 22. 2008. pp. 10215-10220, vol. 105, No. 29.
Hu, X., et al., "Autocatalytic Intramolecular Isopeptide Bond Formation in Gram-Positive Bacterial Pill: A QM/MM Simulation", "J. Am. Chem. Soc.", Dec. 13, 2010, pp. 478-485, vol. 133, No. 3.
Izore, T., et al., "Structural Basis of Host Cell Recognition by the Pilus Adhesin from *Streptococcus pneumoniae*", "Structure", Jan. 13, 2010, pp. 106-115, vol. 18.
Krishnan, V., et al., "An IgG-like Domain in the Minor Pilin GIBS52 of *Streptococcus agalactiae* Mediates Lung Epithelial Cell Adheson", "Structure", Aug. 2007, pp. 893-903, vol. 15.
Miller, A., et al., "Crystal Structure of the Human Two-Pore Domain Potassium Channel K2P1", "Science", Jan. 27, 2012, pp. 432-436, vol. 335.
Mortaji, L, et al., "Stability and Assembly of Pilus Subunits of *Streptococcus pneumoniae*","Journal of Biological Chemistry", Feb. 10, 2010, pp. 12405-12415, vol. 285, No. 16.
Sambrook, J., et al., "Molecular Cloning: A Laboratory Manual: Second Edition", 1989, pp. v-xxxii (Table of Contents only), Publisher: Cold Spring Harbor Laboratory Press, Published in: US.
Wikoff, W., et al., "Topilogically Linked Protein Rings in the Bacteriophage HK97 Capsid", "Science", Sep. 22, 2000, pp. 2129-2133, vol. 289.
Zakfri, B., et al., "Spontaneous Intermolecular Amide Bond Formation between Side Chains for Ineversible Peptide Targeting", "J. Am. Chem. Soc.", Mar. 17, 2010, pp. 4526-4527, vol. 132.

* cited by examiner

*Primary Examiner* — Rodney P Swartz
(74) *Attorney, Agent, or Firm* — Hultquist, PLLC; Mary B. Grant

(57) ABSTRACT

The present invention relates to a peptide capable of forming a covalent complex consisting either of the Jo peptide, a derivative or a fragment thereof, or of the In peptide, a derivative or a fragment thereof. The present invention relates to the various uses thereof.

14 Claims, 8 Drawing Sheets

SEQUENCE LISTING

```
<160> NUMBER OF SEQ ID NOS: 22

<210> SEQ ID NO 1
<211> LENGTH: 225
<212> TYPE: DNA
<213> ORGANISM: Streptococcus pneumoniae
<220> FEATURE:
<221> NAME/KEY: CDS
<222> LOCATION: (1)..(225)
<223> OTHER INFORMATION: Sequence coding Jo peptide

<400> SEQUENCE: 1

cag tat cca caa aca ggg act tat cca gat gtt caa aca cct tat cag       48
Gln Tyr Pro Gln Thr Gly Thr Tyr Pro Asp Val Gln Thr Pro Tyr Gln
1               5                   10                  15

att att aag gta gat ggt tcg gaa aaa aac gga cag cac aag gcg ttg       96
Ile Ile Lys Val Asp Gly Ser Glu Lys Asn Gly Gln His Lys Ala Leu
            20                  25                  30

aat ccg aat cca tat gaa cgt gtg att cca gaa ggt aca ctt tca aag      144
Asn Pro Asn Pro Tyr Glu Arg Val Ile Pro Glu Gly Thr Leu Ser Lys
        35                  40                  45

aga att tat caa gtg aat aat ttg gat gat aac caa tat gga atc gaa      192
Arg Ile Tyr Gln Val Asn Asn Leu Asp Asp Asn Gln Tyr Gly Ile Glu
    50                  55                  60

ttg acg gtt agt ggg aaa aca gtg tat gaa caa                          225
Leu Thr Val Ser Gly Lys Thr Val Tyr Glu Gln
65                  70                  75


<210> SEQ ID NO 2
<211> LENGTH: 75
<212> TYPE: PRT
<213> ORGANISM: Streptococcus pneumoniae

<400> SEQUENCE: 2

Gln Tyr Pro Gln Thr Gly Thr Tyr Pro Asp Val Gln Thr Pro Tyr Gln
1               5                   10                  15

Ile Ile Lys Val Asp Gly Ser Glu Lys Asn Gly Gln His Lys Ala Leu
            20                  25                  30

Asn Pro Asn Pro Tyr Glu Arg Val Ile Pro Glu Gly Thr Leu Ser Lys
        35                  40                  45

Arg Ile Tyr Gln Val Asn Asn Leu Asp Asp Asn Gln Tyr Gly Ile Glu
    50                  55                  60

Leu Thr Val Ser Gly Lys Thr Val Tyr Glu Gln
65                  70                  75


<210> SEQ ID NO 3
<211> LENGTH: 390
<212> TYPE: DNA
<213> ORGANISM: Streptococcus pneumoniae
<220> FEATURE:
<221> NAME/KEY: CDS
<222> LOCATION: (1)..(384)
<223> OTHER INFORMATION: Sequence coding In peptide

<400> SEQUENCE: 3

att gag aat ggt acg att aca gat ccg atg ggt gag tta att gat ttg       48
Ile Glu Asn Gly Thr Ile Thr Asp Pro Met Gly Glu Leu Ile Asp Leu
1               5                   10                  15

caa ttg ggc aca gat gga aga ttt gat cca gca gat tac act tta act       96
Gln Leu Gly Thr Asp Gly Arg Phe Asp Pro Ala Asp Tyr Thr Leu Thr
            20                  25                  30

gca aac gat ggt agt cgc ttg gag aat gga caa gct gta ggt ggt cca      144
Ala Asn Asp Gly Ser Arg Leu Glu Asn Gly Gln Ala Val Gly Gly Pro
```

```
        35                  40                  45

caa aat gat ggt ggt ttg tta aaa aat gca aaa gtg ctc tat gat acg      192
Gln Asn Asp Gly Gly Leu Leu Lys Asn Ala Lys Val Leu Tyr Asp Thr
    50                  55                  60

act gag aaa agg att cgt gta aca ggt ctg tac ctt gga acg gat gaa      240
Thr Glu Lys Arg Ile Arg Val Thr Gly Leu Tyr Leu Gly Thr Asp Glu
65                  70                  75                  80

aaa gtt acg ttg acc tac aat gtt cgt ttg aat gat gag ttt gta agc      288
Lys Val Thr Leu Thr Tyr Asn Val Arg Leu Asn Asp Glu Phe Val Ser
                85                  90                  95

aat aaa ttt tat gat acc aat ggt cga aca acc tta cat cct aag gaa      336
Asn Lys Phe Tyr Asp Thr Asn Gly Arg Thr Thr Leu His Pro Lys Glu
            100                 105                 110

gta gaa cag aac aca gtg cgc gac ttc ccg att cct aag att cgt gat      384
Val Glu Gln Asn Thr Val Arg Asp Phe Pro Ile Pro Lys Ile Arg Asp
        115                 120                 125

cgtgat                                                               390


<210> SEQ ID NO 4
<211> LENGTH: 128
<212> TYPE: PRT
<213> ORGANISM: Streptococcus pneumoniae

<400> SEQUENCE: 4

Ile Glu Asn Gly Thr Ile Thr Asp Pro Met Gly Glu Leu Ile Asp Leu
1               5                   10                  15

Gln Leu Gly Thr Asp Gly Arg Phe Asp Pro Ala Asp Tyr Thr Leu Thr
            20                  25                  30

Ala Asn Asp Gly Ser Arg Leu Glu Asn Gly Gln Ala Val Gly Gly Pro
        35                  40                  45

Gln Asn Asp Gly Gly Leu Leu Lys Asn Ala Lys Val Leu Tyr Asp Thr
    50                  55                  60

Thr Glu Lys Arg Ile Arg Val Thr Gly Leu Tyr Leu Gly Thr Asp Glu
65                  70                  75                  80

Lys Val Thr Leu Thr Tyr Asn Val Arg Leu Asn Asp Glu Phe Val Ser
                85                  90                  95

Asn Lys Phe Tyr Asp Thr Asn Gly Arg Thr Thr Leu His Pro Lys Glu
            100                 105                 110

Val Glu Gln Asn Thr Val Arg Asp Phe Pro Ile Pro Lys Ile Arg Asp
        115                 120                 125


<210> SEQ ID NO 5
<211> LENGTH: 237
<212> TYPE: DNA
<213> ORGANISM: Unknown
<220> FEATURE:
<223> OTHER INFORMATION: Artificial sequence
<220> FEATURE:
<221> NAME/KEY: CDS
<222> LOCATION: (1)..(237)
<223> OTHER INFORMATION: Sequence coding a derivative of Jo peptide

<400> SEQUENCE: 5

tct gac cag tat cca caa aca ggg act tat cca gat gtt caa aca cct       48
Ser Asp Gln Tyr Pro Gln Thr Gly Thr Tyr Pro Asp Val Gln Thr Pro
1               5                   10                  15

tat cag att att aag gta gat ggt tcg gaa aaa aac gga cag cac aag       96
Tyr Gln Ile Ile Lys Val Asp Gly Ser Glu Lys Asn Gly Gln His Lys
            20                  25                  30

gcg ttg aat ccg aat cca tat gaa cgt gtg att cca gaa ggt aca ctt      144
```

-continued

```
Ala Leu Asn Pro Asn Pro Tyr Glu Arg Val Ile Pro Glu Gly Thr Leu
        35                  40                  45

tca aag aga att tat caa gtg aat aat ttg gat gat aac caa tat gga      192
Ser Lys Arg Ile Tyr Gln Val Asn Asn Leu Asp Asp Asn Gln Tyr Gly
    50                  55                  60

atc gaa ttg acg gtt agt ggg aaa aca gtg tat gaa caa aaa gat          237
Ile Glu Leu Thr Val Ser Gly Lys Thr Val Tyr Glu Gln Lys Asp
65                  70                  75


<210> SEQ ID NO 6
<211> LENGTH: 79
<212> TYPE: PRT
<213> ORGANISM: Unknown
<220> FEATURE:
<223> OTHER INFORMATION: Synthetic Construct

<400> SEQUENCE: 6

Ser Asp Gln Tyr Pro Gln Thr Gly Thr Tyr Pro Asp Val Gln Thr Pro
1               5                   10                  15

Tyr Gln Ile Ile Lys Val Asp Gly Ser Glu Lys Asn Gly Gln His Lys
            20                  25                  30

Ala Leu Asn Pro Asn Pro Tyr Glu Arg Val Ile Pro Glu Gly Thr Leu
        35                  40                  45

Ser Lys Arg Ile Tyr Gln Val Asn Asn Leu Asp Asp Asn Gln Tyr Gly
    50                  55                  60

Ile Glu Leu Thr Val Ser Gly Lys Thr Val Tyr Glu Gln Lys Asp
65                  70                  75


<210> SEQ ID NO 7
<211> LENGTH: 399
<212> TYPE: DNA
<213> ORGANISM: Unknown
<220> FEATURE:
<223> OTHER INFORMATION: Artificial sequence
<220> FEATURE:
<221> NAME/KEY: CDS
<222> LOCATION: (1)..(399)
<223> OTHER INFORMATION: Sequence coding a derivative of In peptide

<400> SEQUENCE: 7

act gaa aag aaa tca att gag aat ggt acg att aca gat ccg atg ggt       48
Thr Glu Lys Lys Ser Ile Glu Asn Gly Thr Ile Thr Asp Pro Met Gly
1               5                   10                  15

gag tta att gat ttg caa ttg ggc aca gat gga aga ttt gat cca gca       96
Glu Leu Ile Asp Leu Gln Leu Gly Thr Asp Gly Arg Phe Asp Pro Ala
            20                  25                  30

gat tac act tta act gca aac gat ggt agt cgc ttg gag aat gga caa      144
Asp Tyr Thr Leu Thr Ala Asn Asp Gly Ser Arg Leu Glu Asn Gly Gln
        35                  40                  45

gct gta ggt ggt cca caa aat gat ggt ggt ttg tta aaa aat gca aaa      192
Ala Val Gly Gly Pro Gln Asn Asp Gly Gly Leu Leu Lys Asn Ala Lys
    50                  55                  60

gtg ctc tat gat acg act gag aaa agg att cgt gta aca ggt ctg tac      240
Val Leu Tyr Asp Thr Thr Glu Lys Arg Ile Arg Val Thr Gly Leu Tyr
65                  70                  75                  80

ctt gga acg gat gaa aaa gtt acg ttg acc tac aat gtt cgt ttg aat      288
Leu Gly Thr Asp Glu Lys Val Thr Leu Thr Tyr Asn Val Arg Leu Asn
                85                  90                  95

gat gag ttt gta agc aat aaa ttt tat gat acc aat ggt cga aca acc      336
Asp Glu Phe Val Ser Asn Lys Phe Tyr Asp Thr Asn Gly Arg Thr Thr
            100                 105                 110

tta cat cct aag gaa gta gaa cag aac aca gtg cgc gac ttc ccg att      384
```

```
Leu His Pro Lys Glu Val Glu Gln Asn Thr Val Arg Asp Phe Pro Ile
        115                 120                 125

cct aag att cgt gat                                              399
Pro Lys Ile Arg Asp
    130


<210> SEQ ID NO 8
<211> LENGTH: 133
<212> TYPE: PRT
<213> ORGANISM: Unknown
<220> FEATURE:
<223> OTHER INFORMATION: Synthetic Construct

<400> SEQUENCE: 8

Thr Glu Lys Lys Ser Ile Glu Asn Gly Thr Ile Thr Asp Pro Met Gly
1               5                   10                  15

Glu Leu Ile Asp Leu Gln Leu Gly Thr Asp Gly Arg Phe Asp Pro Ala
            20                  25                  30

Asp Tyr Thr Leu Thr Ala Asn Asp Gly Ser Arg Leu Glu Asn Gly Gln
        35                  40                  45

Ala Val Gly Gly Pro Gln Asn Asp Gly Gly Leu Leu Lys Asn Ala Lys
    50                  55                  60

Val Leu Tyr Asp Thr Thr Glu Lys Arg Ile Arg Val Thr Gly Leu Tyr
65                  70                  75                  80

Leu Gly Thr Asp Glu Lys Val Thr Leu Thr Tyr Asn Val Arg Leu Asn
                85                  90                  95

Asp Glu Phe Val Ser Asn Lys Phe Tyr Asp Thr Asn Gly Arg Thr Thr
            100                 105                 110

Leu His Pro Lys Glu Val Glu Gln Asn Thr Val Arg Asp Phe Pro Ile
        115                 120                 125

Pro Lys Ile Arg Asp
    130


<210> SEQ ID NO 9
<211> LENGTH: 92
<212> TYPE: PRT
<213> ORGANISM: Unknown
<220> FEATURE:
<223> OTHER INFORMATION: Artificial sequence
<220> FEATURE:
<221> NAME/KEY: PEPTIDE
<222> LOCATION: (1)..(92)
<223> OTHER INFORMATION: Peptide HisJo

<400> SEQUENCE: 9

Gly Ser Ser His His His His His His Ser Gln Asp Pro Ser Asp Gln
1               5                   10                  15

Tyr Pro Gln Thr Gly Thr Tyr Pro Asp Val Gln Thr Pro Tyr Gln Ile
            20                  25                  30

Ile Lys Val Asp Gly Ser Glu Lys Asn Gly Gln His Lys Ala Leu Asn
        35                  40                  45

Pro Asn Pro Tyr Glu Arg Val Ile Pro Glu Gly Thr Leu Ser Lys Arg
    50                  55                  60

Ile Tyr Gln Val Asn Asn Leu Asp Asp Asn Gln Tyr Gly Ile Glu Leu
65                  70                  75                  80

Thr Val Ser Gly Lys Thr Val Tyr Glu Gln Lys Asp
                85                  90


<210> SEQ ID NO 10
<211> LENGTH: 146
```

<212> TYPE: PRT
<213> ORGANISM: Unknown
<220> FEATURE:
<223> OTHER INFORMATION: Artificial sequence
<220> FEATURE:
<221> NAME/KEY: PEPTIDE
<222> LOCATION: (1)..(146)
<223> OTHER INFORMATION: Peptide HisIn

<400> SEQUENCE: 10

```
Gly Ser Ser His His His His His His Ser Gln Asp Pro Thr Glu Lys
1               5                   10                  15

Lys Ser Ile Glu Asn Gly Thr Ile Thr Asp Pro Met Gly Glu Leu Ile
            20                  25                  30

Asp Leu Gln Leu Gly Thr Asp Gly Arg Phe Asp Pro Ala Asp Tyr Thr
        35                  40                  45

Leu Thr Ala Asn Asp Gly Ser Arg Leu Glu Asn Gly Gln Ala Val Gly
    50                  55                  60

Gly Pro Gln Asn Asp Gly Gly Leu Leu Lys Asn Ala Lys Val Leu Tyr
65                  70                  75                  80

Asp Thr Thr Glu Lys Arg Ile Arg Val Thr Gly Leu Tyr Leu Gly Thr
                85                  90                  95

Asp Glu Lys Val Thr Leu Thr Tyr Asn Val Arg Leu Asn Asp Glu Phe
            100                 105                 110

Val Ser Asn Lys Phe Tyr Asp Thr Asn Gly Arg Thr Thr Leu His Pro
        115                 120                 125

Lys Glu Val Glu Gln Asn Thr Val Arg Asp Phe Pro Ile Pro Lys Ile
    130                 135                 140

Arg Asp
145
```

<210> SEQ ID NO 11
<211> LENGTH: 228
<212> TYPE: PRT
<213> ORGANISM: Unknown
<220> FEATURE:
<223> OTHER INFORMATION: Artificial sequence
<220> FEATURE:
<221> NAME/KEY: PEPTIDE
<222> LOCATION: (1)..(228)
<223> OTHER INFORMATION: Peptide HisJoIn

<400> SEQUENCE: 11

```
Gly Ser Ser His His His His His His Ser Gln Asp Pro Ser Asp Gln
1               5                   10                  15

Tyr Pro Gln Thr Gly Thr Tyr Pro Asp Val Gln Thr Pro Tyr Gln Ile
            20                  25                  30

Ile Lys Val Asp Gly Ser Glu Lys Asn Gly Gln His Lys Ala Leu Asn
        35                  40                  45

Pro Asn Pro Tyr Glu Arg Val Ile Pro Glu Gly Thr Leu Ser Lys Arg
    50                  55                  60

Ile Tyr Gln Val Asn Asn Leu Asp Asp Asn Gln Tyr Gly Ile Glu Leu
65                  70                  75                  80

Thr Val Ser Gly Lys Thr Val Tyr Glu Gln Lys Asp Ala Asp Leu Thr
                85                  90                  95

Glu Lys Lys Ser Ile Glu Asn Gly Thr Ile Thr Asp Pro Met Gly Glu
            100                 105                 110

Leu Ile Asp Leu Gln Leu Gly Thr Asp Gly Arg Phe Asp Pro Ala Asp
        115                 120                 125
```

Tyr Thr Leu Thr Ala Asn Asp Gly Ser Arg Leu Glu Asn Gly Gln Ala
    130                 135                 140

Val Gly Gly Pro Gln Asn Asp Gly Gly Leu Leu Lys Asn Ala Lys Val
145                 150                 155                 160

Leu Tyr Asp Thr Thr Glu Lys Arg Ile Arg Val Thr Gly Leu Tyr Leu
                165                 170                 175

Gly Thr Asp Glu Lys Val Thr Leu Thr Tyr Asn Val Arg Leu Asn Asp
            180                 185                 190

Glu Phe Val Ser Asn Lys Phe Tyr Asp Thr Asn Gly Arg Thr Thr Leu
        195                 200                 205

His Pro Lys Glu Val Glu Gln Asn Thr Val Arg Asp Phe Pro Ile Pro
    210                 215                 220

Lys Ile Arg Asp
225

<210> SEQ ID NO 12
<211> LENGTH: 239
<212> TYPE: PRT
<213> ORGANISM: Unknown
<220> FEATURE:
<223> OTHER INFORMATION: Artificial sequence
<220> FEATURE:
<221> NAME/KEY: PEPTIDE
<222> LOCATION: (1)..(239)
<223> OTHER INFORMATION: Peptide HisJoHisIn

<400> SEQUENCE: 12

Gly Ser Ser His His His His His His Ser Gln Asp Pro Ser Asp Gln
1               5                   10                  15

Tyr Pro Gln Thr Gly Thr Tyr Pro Asp Val Gln Thr Pro Tyr Gln Ile
            20                  25                  30

Ile Lys Val Asp Gly Ser Glu Lys Asn Gly Gln His Lys Ala Leu Asn
        35                  40                  45

Pro Asn Pro Tyr Glu Arg Val Ile Pro Glu Gly Thr Leu Ser Lys Arg
    50                  55                  60

Ile Tyr Gln Val Asn Asn Leu Asp Asp Asn Gln Tyr Gly Ile Glu Leu
65                  70                  75                  80

Thr Val Ser Gly Lys Thr Val Tyr Glu Gln Lys Asp Met Gly Ser Ser
                85                  90                  95

His His His His His His Ser Gln Asp Pro Thr Glu Lys Lys Ser Ile
            100                 105                 110

Glu Asn Gly Thr Ile Thr Asp Pro Met Gly Glu Leu Ile Asp Leu Gln
        115                 120                 125

Leu Gly Thr Asp Gly Arg Phe Asp Pro Ala Asp Tyr Thr Leu Thr Ala
    130                 135                 140

Asn Asp Gly Ser Arg Leu Glu Asn Gly Gln Ala Val Gly Gly Pro Gln
145                 150                 155                 160

Asn Asp Gly Gly Leu Leu Lys Asn Ala Lys Val Leu Tyr Asp Thr Thr
                165                 170                 175

Glu Lys Arg Ile Arg Val Thr Gly Leu Tyr Leu Gly Thr Asp Glu Lys
            180                 185                 190

Val Thr Leu Thr Tyr Asn Val Arg Leu Asn Asp Glu Phe Val Ser Asn
        195                 200                 205

Lys Phe Tyr Asp Thr Asn Gly Arg Thr Thr Leu His Pro Lys Glu Val
    210                 215                 220

Glu Gln Asn Thr Val Arg Asp Phe Pro Ile Pro Lys Ile Arg Asp
225                 230                 235

<210> SEQ ID NO 13
<211> LENGTH: 232
<212> TYPE: PRT
<213> ORGANISM: Unknown
<220> FEATURE:
<223> OTHER INFORMATION: Artificial sequence
<220> FEATURE:
<221> NAME/KEY: PEPTIDE
<222> LOCATION: (1)..(232)
<223> OTHER INFORMATION: Peptide FusJoIn

<400> SEQUENCE: 13

```
Gly Ser Ser His His His His His His Ser Gln Asp Pro Ser Asp Gln
1               5                   10                  15

Tyr Pro Gln Thr Gly Thr Tyr Pro Asp Val Gln Thr Pro Tyr Gln Ile
            20                  25                  30

Ile Lys Val Asp Gly Ser Glu Lys Asn Gly Gln His Lys Ala Leu Asn
        35                  40                  45

Pro Asn Pro Tyr Glu Arg Val Ile Pro Glu Gly Thr Leu Ser Lys Arg
    50                  55                  60

Ile Tyr Gln Val Asn Asn Leu Asp Asp Asn Gln Tyr Gly Ile Glu Leu
65                  70                  75                  80

Thr Val Ser Gly Lys Thr Val Tyr Glu Gln Lys Asp Gly Ser Thr Pro
                85                  90                  95

Gly Ser Val Thr Glu Lys Lys Ser Ile Glu Asn Gly Thr Ile Thr Asp
            100                 105                 110

Pro Met Gly Glu Leu Ile Asp Leu Gln Leu Gly Thr Asp Gly Arg Phe
        115                 120                 125

Asp Pro Ala Asp Tyr Thr Leu Thr Ala Asn Asp Gly Ser Arg Leu Glu
    130                 135                 140

Asn Gly Gln Ala Val Gly Gly Pro Gln Asn Asp Gly Gly Leu Leu Lys
145                 150                 155                 160

Asn Ala Lys Val Leu Tyr Asp Thr Thr Glu Lys Arg Ile Arg Val Thr
                165                 170                 175

Gly Leu Tyr Leu Gly Thr Asp Glu Lys Val Thr Leu Thr Tyr Asn Val
            180                 185                 190

Arg Leu Asn Asp Glu Phe Val Ser Asn Lys Phe Tyr Asp Thr Asn Gly
        195                 200                 205

Arg Thr Thr Leu His Pro Lys Glu Val Glu Gln Asn Thr Val Arg Asp
    210                 215                 220

Phe Pro Ile Pro Lys Ile Arg Asp
225                 230
```

<210> SEQ ID NO 14
<211> LENGTH: 86
<212> TYPE: DNA
<213> ORGANISM: Unknown
<220> FEATURE:
<223> OTHER INFORMATION: Sequence in the plasmid derived from pET-Duet-1
<220> FEATURE:
<221> NAME/KEY: misc_feature
<222> LOCATION: (1)..(35)
<223> OTHER INFORMATION: Partial sequence of a derivative of Jo
<220> FEATURE:
<221> NAME/KEY: CDS
<222> LOCATION: (36)..(56)
<223> OTHER INFORMATION: Sequence coding a 7 amino acid linker
<220> FEATURE:
<221> NAME/KEY: misc_feature
<222> LOCATION: (57)..(86)
<223> OTHER INFORMATION: Partial sequence of a derivative of In

<400> SEQUENCE: 14

```
cggttagtgg gaaaacagtg tatgaacaaa aagat ggt tct acc ccg ggt tct        53
                                       Gly Ser Thr Pro Gly Ser
                                       1               5

gtt actgaaaaga aatcaattga gaatggtacg                                  86
Val
```

<210> SEQ ID NO 15
<211> LENGTH: 7
<212> TYPE: PRT
<213> ORGANISM: Unknown
<220> FEATURE:
<223> OTHER INFORMATION: Synthetic Construct

<400> SEQUENCE: 15

```
Gly Ser Thr Pro Gly Ser Val
1               5
```

<210> SEQ ID NO 16
<211> LENGTH: 98
<212> TYPE: DNA
<213> ORGANISM: Unknown
<220> FEATURE:
<223> OTHER INFORMATION: Oligomer 1

<400> SEQUENCE: 16

```
cggttagtgg gaaaacagtg tatgaacaaa aagatggaat tcggtacccc tgcagggagc     60

tgaagcttac tgaaaagaaa tcaattgaga atggtacg                             98
```

<210> SEQ ID NO 17
<211> LENGTH: 98
<212> TYPE: DNA
<213> ORGANISM: Unknown
<220> FEATURE:
<223> OTHER INFORMATION: Oligomer 2

<400> SEQUENCE: 17

```
cgtaccattc tcaattgatt tcttttcagt aagcttcagc tccctgcagg ggtaccgaat     60

tccatctttt tgttcataca ctgttttccc actaaccg                             98
```

<210> SEQ ID NO 18
<211> LENGTH: 30
<212> TYPE: DNA
<213> ORGANISM: Unknown
<220> FEATURE:
<223> OTHER INFORMATION: Oligomer 3

<400> SEQUENCE: 18

```
gcgcgaattc cagaaatttc tcagcgtacg                                      30
```

<210> SEQ ID NO 19
<211> LENGTH: 27
<212> TYPE: DNA
<213> ORGANISM: Unknown
<220> FEATURE:
<223> OTHER INFORMATION: Oligomer 4

<400> SEQUENCE: 19

```
gcgcaagctt gctgatttgg tttgatg                                         27
```

<210> SEQ ID NO 20
<211> LENGTH: 756
<212> TYPE: DNA

<213> ORGANISM: Unknown
<220> FEATURE:
<223> OTHER INFORMATION: Nucleotide sequence of the relevant region of the cloning vector enabling the expression of a fusion protein having the Jo and In derivatives respectively in N- and C-terminus of the protein
<220> FEATURE:
<221> NAME/KEY: misc_feature
<222> LOCATION: (43)..(60)
<223> OTHER INFORMATION: Nucleotide sequence coding 6 histidines
<220> FEATURE:
<221> NAME/KEY: misc_feature
<222> LOCATION: (73)..(309)
<223> OTHER INFORMATION: Nucleotide sequence coding a derivative of Jo
<220> FEATURE:
<221> NAME/KEY: misc_feature
<222> LOCATION: (310)..(342)
<223> OTHER INFORMATION: Multiple cloning site (5 restriction sites)
<220> FEATURE:
<221> NAME/KEY: misc_feature
<222> LOCATION: (311)..(316)
<223> OTHER INFORMATION: Restriction site EcoRI
<220> FEATURE:
<221> NAME/KEY: misc_feature
<222> LOCATION: (317)..(322)
<223> OTHER INFORMATION: Restriction site KpnI
<220> FEATURE:
<221> NAME/KEY: misc_feature
<222> LOCATION: (324)..(329)
<223> OTHER INFORMATION: Restriction site PstI
<220> FEATURE:
<221> NAME/KEY: misc_feature
<222> LOCATION: (331)..(336)
<223> OTHER INFORMATION: Restriction site SacI
<220> FEATURE:
<221> NAME/KEY: misc_feature
<222> LOCATION: (337)..(342)
<223> OTHER INFORMATION: Restriction site HindIII
<220> FEATURE:
<221> NAME/KEY: misc_feature
<222> LOCATION: (343)..(744)
<223> OTHER INFORMATION: Nucleotide sequence coding a derivative of In

<400> SEQUENCE: 20

```
ttttgtttaa ctttaagaag gagatatacc atgggcagca gccatcacca tcatcaccac     60

agccaggatc cgtctgacca gtatccacaa acagggactt atccagatgt tcaaacacct    120

tatcagatta ttaaggtaga tggttcggaa aaaaacggac agcacaaggc gttgaatccg    180

aatccatatg aacgtgtgat tccagaaggt acactttcaa agagaattta tcaagtgaat    240

aatttggatg ataaccaata tggaatcgaa ttgacggtta gtgggaaaac agtgtatgaa    300

caaaaagatg gaattcggta cccctgcagg gagctgaagc ttactgaaaa gaaatcaatt    360

gagaatggta cgattacaga tccgatgggt gagttaattg atttgcaatt gggcacagat    420

ggaagatttg atccagcaga ttacacttta actgcaaacg atggtagtcg cttggagaat    480

ggacaagctg taggtggtcc acaaaatgat ggtggtttgt taaaaaatgc aaaagtgctc    540

tatgatacga ctgagaaaag gattcgtgta acaggtctgt accttggaac ggatgaaaaa    600

gttacgttga cctacaatgt tcgtttgaat gatgagtttg taagcaataa attttatgat    660

accaatggtc gaacaacctt acatcctaag gaagtagaac agaacacagt gcgcgacttc    720

ccgattccta agattcgtga ttgactcgag tctggt                              756
```

<210> SEQ ID NO 21
<211> LENGTH: 867
<212> TYPE: DNA
<213> ORGANISM: Unknown
<220> FEATURE:
<223> OTHER INFORMATION: Nucleotide sequence of the relevant region of the vector enabling the expression of a fusion protein having the

```
      Jo and In derivatives localized respectively in N- and C-terminus
      of loop 1 of the potassium channel
<220> FEATURE:
<221> NAME/KEY: CDS
<222> LOCATION: (1)..(855)
<220> FEATURE:
<221> NAME/KEY: misc_feature
<222> LOCATION: (13)..(30)
<223> OTHER INFORMATION: Nucleotide sequence coding 6 histidines
<220> FEATURE:
<221> NAME/KEY: misc_feature
<222> LOCATION: (43)..(279)
<223> OTHER INFORMATION: Nucleotide sequence coding a derivative of Jo
<220> FEATURE:
<221> NAME/KEY: misc_feature
<222> LOCATION: (280)..(288)
<223> OTHER INFORMATION: Nucleotide sequence coding the linker amino
      acids
<220> FEATURE:
<221> NAME/KEY: misc_feature
<222> LOCATION: (289)..(447)
<223> OTHER INFORMATION: Nucleotide sequence coding loop 1 of the
      potassium channel
<220> FEATURE:
<221> NAME/KEY: misc_feature
<222> LOCATION: (448)..(453)
<223> OTHER INFORMATION: Nucleotide sequence coding the linker amino
      acids
<220> FEATURE:
<221> NAME/KEY: misc_feature
<222> LOCATION: (454)..(855)
<223> OTHER INFORMATION: Nucleotide sequence coding a derivative of In

<400> SEQUENCE: 21

atg ggc agc agc cat cac cat cat cac cac agc cag gat ccg tct gac       48
Met Gly Ser Ser His His His His His His Ser Gln Asp Pro Ser Asp
1               5                   10                  15

cag tat cca caa aca ggg act tat cca gat gtt caa aca cct tat cag       96
Gln Tyr Pro Gln Thr Gly Thr Tyr Pro Asp Val Gln Thr Pro Tyr Gln
            20                  25                  30

att att aag gta gat ggt tcg gaa aaa aac gga cag cac aag gcg ttg      144
Ile Ile Lys Val Asp Gly Ser Glu Lys Asn Gly Gln His Lys Ala Leu
        35                  40                  45

aat ccg aat cca tat gaa cgt gtg att cca gaa ggt aca ctt tca aag      192
Asn Pro Asn Pro Tyr Glu Arg Val Ile Pro Glu Gly Thr Leu Ser Lys
    50                  55                  60

aga att tat caa gtg aat aat ttg gat gat aac caa tat gga atc gaa      240
Arg Ile Tyr Gln Val Asn Asn Leu Asp Asp Asn Gln Tyr Gly Ile Glu
65                  70                  75                  80

ttg acg gtt agt ggg aaa aca gtg tat gaa caa aaa gat gga att cca      288
Leu Thr Val Ser Gly Lys Thr Val Tyr Glu Gln Lys Asp Gly Ile Pro
                85                  90                  95

gaa att tct cag cgt acg acc att gtg att cag aaa caa acg ttt atc      336
Glu Ile Ser Gln Arg Thr Thr Ile Val Ile Gln Lys Gln Thr Phe Ile
            100                 105                 110

agt cag cat tcc tgt gtg aat agc acc gaa ctg gat gaa ctg atc caa      384
Ser Gln His Ser Cys Val Asn Ser Thr Glu Leu Asp Glu Leu Ile Gln
        115                 120                 125

caa att gtg gca gcg atc aat gcc ggt att att cca ctg ggg aac aca      432
Gln Ile Val Ala Ala Ile Asn Ala Gly Ile Ile Pro Leu Gly Asn Thr
    130                 135                 140

tca aac caa atc agc aag ctt act gaa aag aaa tca att gag aat ggt      480
Ser Asn Gln Ile Ser Lys Leu Thr Glu Lys Lys Ser Ile Glu Asn Gly
145                 150                 155                 160

acg att aca gat ccg atg ggt gag tta att gat ttg caa ttg ggc aca      528
Thr Ile Thr Asp Pro Met Gly Glu Leu Ile Asp Leu Gln Leu Gly Thr
                165                 170                 175
```

```
gat gga aga ttt gat cca gca gat tac act tta act gca aac gat ggt      576
Asp Gly Arg Phe Asp Pro Ala Asp Tyr Thr Leu Thr Ala Asn Asp Gly
            180                 185                 190

agt cgc ttg gag aat gga caa gct gta ggt ggt cca caa aat gat ggt      624
Ser Arg Leu Glu Asn Gly Gln Ala Val Gly Gly Pro Gln Asn Asp Gly
        195                 200                 205

ggt ttg tta aaa aat gca aaa gtg ctc tat gat acg act gag aaa agg      672
Gly Leu Leu Lys Asn Ala Lys Val Leu Tyr Asp Thr Thr Glu Lys Arg
    210                 215                 220

att cgt gta aca ggt ctg tac ctt gga acg gat gaa aaa gtt acg ttg      720
Ile Arg Val Thr Gly Leu Tyr Leu Gly Thr Asp Glu Lys Val Thr Leu
225                 230                 235                 240

acc tac aat gtt cgt ttg aat gat gag ttt gta agc aat aaa ttt tat      768
Thr Tyr Asn Val Arg Leu Asn Asp Glu Phe Val Ser Asn Lys Phe Tyr
                245                 250                 255

gat acc aat ggt cga aca acc tta cat cct aag gaa gta gaa cag aac      816
Asp Thr Asn Gly Arg Thr Thr Leu His Pro Lys Glu Val Glu Gln Asn
            260                 265                 270

aca gtg cgc gac ttc ccg att cct aag att cgt gat tga ctcgagtctg gt    867
Thr Val Arg Asp Phe Pro Ile Pro Lys Ile Arg Asp
        275                 280


<210> SEQ ID NO 22
<211> LENGTH: 284
<212> TYPE: PRT
<213> ORGANISM: Unknown
<220> FEATURE:
<223> OTHER INFORMATION: Synthetic Construct

<400> SEQUENCE: 22

Met Gly Ser Ser His His His His His His Ser Gln Asp Pro Ser Asp
1               5                   10                  15

Gln Tyr Pro Gln Thr Gly Thr Tyr Pro Asp Val Gln Thr Pro Tyr Gln
            20                  25                  30

Ile Ile Lys Val Asp Gly Ser Glu Lys Asn Gly Gln His Lys Ala Leu
        35                  40                  45

Asn Pro Asn Pro Tyr Glu Arg Val Ile Pro Glu Gly Thr Leu Ser Lys
    50                  55                  60

Arg Ile Tyr Gln Val Asn Asn Leu Asp Asp Asn Gln Tyr Gly Ile Glu
65                  70                  75                  80

Leu Thr Val Ser Gly Lys Thr Val Tyr Glu Gln Lys Asp Gly Ile Pro
                85                  90                  95

Glu Ile Ser Gln Arg Thr Thr Ile Val Ile Gln Lys Gln Thr Phe Ile
            100                 105                 110

Ser Gln His Ser Cys Val Asn Ser Thr Glu Leu Asp Glu Leu Ile Gln
        115                 120                 125

Gln Ile Val Ala Ala Ile Asn Ala Gly Ile Ile Pro Leu Gly Asn Thr
    130                 135                 140

Ser Asn Gln Ile Ser Lys Leu Thr Glu Lys Lys Ser Ile Glu Asn Gly
145                 150                 155                 160

Thr Ile Thr Asp Pro Met Gly Glu Leu Ile Asp Leu Gln Leu Gly Thr
                165                 170                 175

Asp Gly Arg Phe Asp Pro Ala Asp Tyr Thr Leu Thr Ala Asn Asp Gly
            180                 185                 190

Ser Arg Leu Glu Asn Gly Gln Ala Val Gly Gly Pro Gln Asn Asp Gly
        195                 200                 205

Gly Leu Leu Lys Asn Ala Lys Val Leu Tyr Asp Thr Thr Glu Lys Arg
    210                 215                 220
```

-continued

```
Ile Arg Val Thr Gly Leu Tyr Leu Gly Thr Asp Glu Lys Val Thr Leu
225                 230                 235                 240

Thr Tyr Asn Val Arg Leu Asn Asp Glu Phe Val Ser Asn Lys Phe Tyr
                245                 250                 255

Asp Thr Asn Gly Arg Thr Thr Leu His Pro Lys Glu Val Glu Gln Asn
            260                 265                 270

Thr Val Arg Asp Phe Pro Ile Pro Lys Ile Arg Asp
        275                 280
```

PEPTIDES CAPABLE OF FORMING A CONVALENT COMPLEX, AND USES THEREOF

CROSS-REFERENCE TO RELATED APPLICATIONS

This application is a U.S. national phase under the provisions of 35 U.S.C. §371 of International Patent Application No. PCT/EP12/55333 filed Mar. 26, 2012, which in turn claims priority of French Patent Application No. 1152432 filed Mar. 24, 2011. The disclosures of such international patent application and French priority patent application are hereby incorporated herein by reference in their respective entireties, for all purposes.

TECHNICAL FIELD

The present invention relates to, in a general manner, the field of biotechnologies and particularly the field of tools useful in biotechnology.

More particularly, the present invention proposes two novel peptides, designated hereafter Jo and In, capable of binding to each other in a covalent and irreversible manner and in mild conditions, supplying, hence, tools useful not only in the field of the detection, the purification and the identification of compounds of interest but also in the field of protein engineering.

The present invention also relates to the heterodimer corresponding to the fusion of the Jo and In peptides as well as an element such as a solid support or a compound marked by at least one of the Jo or In peptides and uses thereof.

PRIOR ART

The phenomenon of specific recognition between molecules is the basis for biological systems and is used in numerous biotechnology applications.

This recognition between macromolecules (proteins, nucleic acids) or between macromolecules and organic molecules of smaller size or atoms takes place, in the very great majority of cases, through the intermediary of several non-covalent chemical bonds.

The methods of purification, analysis and detection of such macromolecules also implement such specific recognitions. For example, the latter involve the (strept)avidin/biotin, protein A/immunoglobulin, protein G/immunoglobulin, antibody/antigen couples or antibody/epitope couples such as the poly-His peptide and a specific antibody of said peptide or the C-terminal fragment of the Myc protein and the monoclonal antibody 9E10; enzyme/substrate couples such as the couple glutathione S-transferase/glutathione or nucleotide sequence/complementary nucleotide sequence couples.

Nevertheless, these non-covalent interactions involve ionic bonds, hydrogen bonds, hydrophobic bonds and/or Van der Waals forces. These interactions are thus reversible and non-permanent. Thus, the use and implementation thereof is dependent on the conditions of stringency, temperature and/or pH to which the aforementioned couples are subjected.

The combination of the phenomena of specific recognition of two entities followed by the spontaneous and irreversible bonding thereof by the formation of a covalent bond would be a considerable advantage for a wide range of applications in biotechnology and in the field of innovative materials.

The article by Zakeri and Howarth, 2010 (J. Am. Chem. Soc., vol. 132, pages 4526-4527) proposes a means for binding a peptide label in an irreversible manner by implementing an isopeptide bond i.e. a bond involving the side chain of a lysine and the side chain of an asparagine, non-consecutive. The works described in this article have been carried out on the Spy0128 protein of *Streptococcus pyogenes* having two isopeptide bonds: one between the side chain of Lys179 and the side chain of Asn303 and the other between the side chain of Lys36 and the side chain of Asn168.

The Spy0128 protein has been divided into two fragments: the $1^{st}$ corresponds to the residues 18-299 of the Spy0128 protein and containing Lys179, whereas the other corresponds to the residues 293-308 and contain Asn303. These two fragments produced in a recombinant manner then mixed together are capable of binding together in a covalent manner via the peptide bond between Lys179 and Asn303. This bond is spontaneous, specific and takes place in conditions of pH comprised between 6 and 8 and temperature comprised between 4 and 37° C. The formation of this isopeptide bond between the two fragments has also been shown in vivo. The other isopeptide bond has been studied, in a similar manner, in vitro, by dividing the Spy0128 protein into two fragments each containing one of the amino acids involved in the isopeptide bond.

It should be pointed out that the article by Zakeri and Howarth, 2010 only presents results obtained with fragments that together correspond to the entire or nearly entire Spy0128 protein since only slight modifications of the fragments described are envisaged in this article.

The article by Izoré et al., 2010 (Structure, vol. 18, pages 106-115) relates to the high resolution crystallographic structure of the bacterial protein RrgA (UniProt AC: Q97SC3). This adhesin is associated with the fibrillar structure, described as pilus, present on the surface of the human pathogen bacterium *Streptococcus pneumoniae*. This adhesin is described as an adhesin with 4 structural domains, designated D1, D2, D3 and D4. The globular domain D2 is divided into two regions separated by the domain D3, the $1^{st}$ region corresponding to the amino acids 144-218, and the $2^{nd}$ to the amino acids 593-722, these two regions being respectively designated region H1 and region H2. In the RrgA protein, two intramolecular isopeptide bonds stabilising the structure of the latter have been identified. One of said bonds is situated between Lys742 and Asn854 of the domain D4 and the other between Lys191 and Asn695 binding in fact two amino acids belonging to the two regions of the domain D2 described previously.

The inventors have thus set themselves the aim of proposing peptide compounds enabling a specific, irreversible and spontaneous recognition and in mild conditions and thus compatible with in vivo use.

DESCRIPTION OF THE INVENTION

The present invention makes it possible to resolve the technical problems of the elements used for specific recognition of the prior art and to achieve the aim that the inventors have set themselves.

In fact, the inventors have continued their works on the adhesin RrgA. They have shown that the covalent association capacity between Lys191 and Asn695 is conserved when two particular regions which are the region H1 and the region H2, hereafter respectively designated domain or protein Jo and domain or protein In, are isolated from the RrgA parent protein thereof and produced in recombinant form in the bacterium *E. coli* by genetic engineering methods. This discovery is not trivial because the two domains Jo and In are very far apart in the primary sequence of amino acids of RrgA. It was thus not obvious for those skilled in the art that other elements in the sequence of RrgA are not necessary in the formation of this isopeptide bond, that the latter is maintained in the absence of % of the RrgA protein and that these two isolated domains can form this bond in vitro just as well as in vivo. Similarly, the article by Zakeri and Howarth, 2010 does not in any way suggest working with particular and restricted domains of the Spy0128 protein.

More particularly, the works of the inventors have shown that the association between the Jo and In domains is very specific because unlike the vast majority of molecular interactions in biology, it forms an irreversible covalent bond. Consequently, it is not very probable that by-products resulting from the undesired association of Jo and In with other natural substances appear. This association may take place in vitro or in vivo. The bond between Jo and In is, in addition, covalent and thus irreversible resulting in a very stable complex via the interaction between these domains.

In addition, it has been demonstrated that the bonding reaction between Jo and In is spontaneous and takes place in mild conditions without requiring energy and without addition of costly or complex reagents. Accordingly, this association may be implemented in vitro or in an in vivo cellular context. The inventors have also shown that the covalent association between the Jo and In domains induces a resistance of the complex to proteolysis and to dissociation by heat, dissociation by the action of chaotropic agents, dissociation by modification of the acid-base environment and dissociation by the action of detergents.

Finally, the Jo and In peptides associated together crystallize in robust conditions by implementing concentrations of the order of 10 mg/ml and solutions conventionally used in crystallography. In these conditions, crystals having good diffraction quality are obtained in 2-3 days.

Given the remarkable properties set out above, the JoIn complex constitutes a tool not only in biotechnology, and particularly for immunodetection and purification by affinity, but also in the manufacture of innovative products such as polymers or in crystallography.

The present invention relates to a peptide capable of forming a covalent complex consisting in:

either the peptide, designated Jo peptide, the amino acid sequence of which is the following:

```
    (SEQ ID NO: 2 in the appended sequence listing)
QYPQTGTYPDVQTPYQIIKVDGSEKNGQHKALNPNPYERVIPEGTLSKRI

YQVNNLDDNQYGIELTVSGKTVYEQ,
```

a derivative or a fragment thereof;

or the peptide, designated In peptide, the amino acid sequence of which is the following:

```
    (SEQ ID NO: 4 in the appended sequence listing)
IENGTITDPMGELIDLQLGTDGRFDPADYTLTANDGSRLENGQAVGGPQN

DGGLLKNAKVLYDTTEKRIRVTGLYLGTDEKVTLTYNVRLNDEFVSNKFY

DTNGRTTLHPKEVEQNTVRDFPIPKIRDVR,
```

a derivative or a fragment thereof.

"Peptide capable of forming a covalent complex" is taken to mean, within the scope of the present invention, an entity of peptide nature capable of forming a covalent and irreversible complex when placed in the presence of the peptide partner involved in said complex. The two peptides that are the subject matter of the present invention constitute the two partners from which a complex may be obtained.

The Jo peptide corresponds to the natural sequence comprised between the amino acids 144-218 of RrgA of *Streptococcus pneumoniae* and thus corresponds to the domain defined as the H1 region of RrgA.

The In peptide corresponds to the natural sequence comprised between the amino acids 593-722 of RrgA of *Streptococcus pneumoniae* and thus corresponds to the domain defined as region H2 of RrgA.

In the present, the expressions "Jo peptide", "Jo protein" and "Jo" are equivalent and useable in an interchangeable manner. Similarly, the expressions "In peptide", "In protein" and "In" are equivalent and useable in an interchangeable manner.

"Derivative of the Jo peptide" or "derivative of the In peptide", is taken to mean peptides that have at least 40%, at least 45%, at least 50%, at least 55%, at least 60%, at least 65%, at least 70%, at least 75%, at least 80%, at least 85%, at least 90%, at least 95% and/or at least 99% of identity respectively with the sequences of the Jo peptide and of the In peptide given above. This definition of derivative covers, consequently, the homologues of the Jo and In peptides. "Homologue of the Jo peptide" or "homologue of the In peptide" is taken to mean a different or equivalent form of the Jo peptide or of the In peptide, isolated from a different species of *Streptococcus pneumoniae*. A particular example of such a derivative is a derivative derived from the PiIA protein of *Streptococcus agalactiae*.

"Percentage of identity" between two amino acid sequences (or between two nucleotide sequences as envisaged hereafter), is taken to mean, within the scope of the present invention, an identical percentage of residues of amino acids (or nucleotides) between the two compared sequences, said percentage being obtained after implementation of the best alignment (optimum alignment) between the two sequences. Those skilled in the art know different techniques making it possible to obtain such a percentage of identity and involving homology algorithms or computer programs such as the BLAST program.

The percentage of identity is statistical and the differences between the two sequences are distributed randomly along said sequences. The differences between the two sequences may consist in different types of modifications of sequences: deletions, substitutions or additions of amino acid residues (or of nucleotides).

Thus, the modifications between the Jo and In peptides and derivatives thereof may consist in substitutions, additions and/or deletions of one or more amino acids. The envisaged substitutions can be substitutions between equivalent amino acids i.e. amino acids having structural homologies or not substantially modifying the properties of the Jo peptide or the In peptide. In a variant, the envisaged substitutions can be substitutions by non-equivalent amino acids i.e. amino acids not having structural homology. Whatever the type of modifications implemented, the latter nevertheless do not affect the capacity of a derivative of the Jo peptide (or a derivative of the In peptide) to covalently bind together by means of an isopeptide bond with the In peptide, a fragment or a derivative thereof (or with the Jo peptide, a fragment or a derivative thereof).

The derivatives of the Jo and In peptides may also have, compared to the sequences SEQ ID NO: 2 and SEQ ID NO: 4 given above, at least one additional amino acid in C-terminal part and/or in N-terminal part, a post-translational modification and/or a chemical modification in particular a glycosylation, an amidation, an acylation, a acetylation, a methylation, as well as peptides that bear a protector group which makes it possible to avoid the degradation thereof. Advantageously, the derivatives of the proteins Jo and In may have, compared to the sequences SEQ ID NO: 2 and SEQ ID NO: 4 given above, 1, 2, 3, 4, 5, 6, 7, 8, 9 or 10 additional amino acid(s) in C-terminal part and/or 1, 2, 3, 4, 5, 6, 7, 8, 9 or 10 additional amino acid(s) in N-terminal part. A particular example of such derivatives corresponds to the derivative of the Jo peptide, the amino acid sequence of which is the following:

```
    (SEQ ID NO: 6 in the appended sequence listing)
SDQYPQTGTYPDVQTPYQIIKVDGSEKNGQHKALNPNPYERVIPEGTLSK

RIYQVNNLDDNQYGIELTVSGKTVYEQKD;
```

In a variant, the derivatives of the proteins Jo and In may have, compared to the sequences SEQ ID NO: 2 and SEQ ID NO: 4 given above, 1, 2, 3, 4, 5, 6, 7, 8, 9 or 10 amino acid(s) more in C-terminal part and/or 1, 2, 3, 4, 5, 6, 7, 8, 9 or 10 amino acid(s) less in N-terminal part.

In a further variant, the derivatives of the proteins Jo and In may have, compared to the sequences SEQ ID NO: 2 and SEQ ID NO: 4 given above, 1, 2, 3, 4, 5, 6, 7, 8, 9 or 10 amino acid(s) less in C-terminal part and/or 1, 2, 3, 4, 5, 6, 7, 8, 9 or 10 amino acid(s) more in N-terminal part.

A particular example of such variants is the derivative of the In peptide, the amino acid sequence of which is the following:

```
    (SEQ ID NO: 8 in the appended sequence listing)
TEKKSIENGTITDPMGELIDLQLGTDGRFDPADYTLTANDGSRLENGQAV

GGPQNDGGLLKNAKVLYDTTEKRIRVTGLYLGTDEKVTLTYNVRLNDEFV

SNKFYDTNGRTTLHPKEVEQNTVRDFPIPKIRD.
```

The derivatives of the Jo and In peptides can also be those in which one or more amino acids are selected from the group constituted of enantiomers, diastereoisomers, natural amino acids of D conformation, beta amino acids, alpha substituted amino acids, rare amino acids particularly hydroxyproline, hydroxylysine, allo-hydroxylysine, 6-N-methyllysine, N-ethylglycine, N-methylglycine, N-ethylasparagine, allo-isoleucine, N-methylisoleucine, N-methylvaline, pyroglutamine, aminobutyric acid and synthetic amino acids particularly ornithine, norleucine, norvaline, cyclohexyl-alanine and omega-amino acids. The derivatives of the Jo and In peptides also cover according to the invention retro-peptides and retro-inversopeptides, as well as the peptides of which the side chain of one or more amino acids is substituted by groups that do not modify the recognition and the fusion of a derivative of the Jo peptide with a derivative of the In peptide.

Thus, whatever the type of derivative envisaged, a derivative of the Jo peptide (or a derivative of the In peptide) conserves its capacity to covalently bind together by means of an isopeptide bond with the In peptide, a fragment or a derivative thereof (or with the Jo peptide, a fragment or a derivative thereof).

It is clear that neither the Jo peptide, nor the In peptide, nor any one of the derivatives or fragments thereof covers the RrgA protein or one of the homologues thereof as such.

"Fragment of the Jo peptide" is taken to mean any part or any portion of the Jo peptide having conserved its capacity to covalently bind together by means of an isopeptide bond with the In peptide. A fragment of the Jo peptide has at least one amino acid less in C-terminal part and/or in N-terminal part compared to the sequence SEQ ID NO: 2 in the appended listing of sequences. Advantageously, a fragment of the Jo peptide corresponds to the amino acid sequence comprised:

- between amino acids 146 and 216 of the RrgA protein (i.e. amino acids 3 and 73 of SEQ ID NO: 2 in the appended listing of sequences);
- between amino acids 148 and 214 of the RrgA protein (i.e. amino acids 5 and 71 of SEQ ID NO: 2 in the appended listing of sequences);
- between amino acids 150 and 212 of the RrgA protein (i.e. amino acids 7 and 69 of SEQ ID NO: 2 in the appended listing of sequences);
- between amino acids 160 and 205 of the RrgA protein (i.e. amino acids 17 and 62 of SEQ ID NO: 2 in the appended listing of sequences);
- between amino acids 170 and 200 of the RrgA protein (i.e. amino acids 27 and 57 of SEQ ID NO: 2 in the appended listing of sequences);
- between amino acids 180 and 195 of the RrgA protein (i.e. amino acids 37 and 52 of SEQ ID NO: 2 in the appended listing of sequences).

"Fragment of the In peptide" is taken to mean any part or any portion of the In peptide having conserved its capacity to covalently bind together by means of an isopeptide bond with the Jo peptide. A fragment of the In peptide has at least one amino acid less in C-terminal part and/or in N-terminal part compared to the sequence SEQ ID NO: 4 in the appended listing of sequences. Advantageously, a fragment of the In peptide corresponds to the amino acid sequence comprised:

- between amino acids 595 and 720 of the RrgA protein (i.e. between amino acids 3 and 128 of SEQ ID NO: 4 in the appended listing of sequences);
- between amino acids 596 and 716 of the RrgA protein (i.e. amino acids 4 and 124 of SEQ ID NO: 4 in the appended listing of sequences);
- between amino acids 597 and 712 of the RrgA protein (i.e. between amino acids 5 and 120 of SEQ ID NO: 4 in the appended listing of sequences);
- between amino acids 598 and 708 of the RrgA protein (i.e. amino acids 6 and 116 of SEQ ID NO: 4 in the appended listing of sequences);
- between amino acids 599 and 704 of the RrgA protein (i.e. between amino acids 7 and 112 of SEQ ID NO: 4 in the appended listing of sequences);
- between amino acids 600 and 700 of the RrgA protein (i.e. amino acids 8 and 108 of SEQ ID NO: 4 in the appended listing of sequences).

Thus, whatever the type of fragment envisaged, a fragment of the Jo peptide (or a fragment of the In peptide) conserves its capacity to covalently bind together by means of an isopeptide bond with the In peptide, a fragment or a derivative thereof (or with the Jo peptide, a fragment or a derivative thereof).

According to a particular embodiment, the invention relates to:

- the Jo peptide of sequence SEQ ID NO: 6 above, a derivative or a fragment thereof capable of covalently binding by means of an isopeptide bond to the In peptide (or a fragment or a derivative thereof) and/or the In peptide of sequence SEQ ID NO: 8 above, a derivative or a fragment thereof capable of covalently binding by means of an isopeptide bond to the Jo peptide (or a fragment or a derivative thereof).

The present invention relates to the heterodimer formed by the two peptides of the invention and as defined previously and bound to each other by an isopeptide bond. In other words, said heterodimer comprises the Jo peptide of sequence SEQ ID NO: 2 above, a derivative or a fragment thereof and the In peptide of sequence SEQ ID NO: 4 above, a derivative or a fragment thereof, said Jo and In peptides being bound to each other by an isopeptide bond.

This aspect of the present invention covers more particularly a heterodimer comprising:

the Jo peptide and the In peptide bound to each other by an isopeptide bond;

a derivative of the Jo peptide and a derivative of the In peptide, bound to each other by an isopeptide bond;

a fragment of the Jo peptide and a fragment of the In peptide, bound to each other by an isopeptide bond;

a derivative of the Jo (or In) peptide and the In (or Jo) peptide bound to each other by an isopeptide bond;

a fragment of the Jo (or In) peptide and the In (or Jo) peptide bound to each other by an isopeptide bond; and a derivative of the Jo (or In) peptide and a fragment of the In (or Jo) peptide bound to each other by an isopeptide bond.

It is also clear that the heterodimer that is the subject matter of the present invention consists in the isolated heterodimer and thus does not cover the heterodimer naturally included in the RrgA protein or one of the homologues thereof.

The present invention also relates to an isolated polynucleotide selected from the different polynucleotides hereafter:

i) a polynucleotide encoding a peptide according to the invention as defined previously;

ii) a complementary polynucleotide of the polynucleotide as defined in point (i);

iii) a polynucleotide of at least 18 nucleotides, capable of hybridizing itself in conditions of high stringency to the polynucleotides as defined in points (i) and (ii).

The polynucleotide according to the invention does not correspond to a nucleotide sequence in the natural state thereof i.e. in the natural chromosomal environment thereof. The polynucleotide does not correspond either to the natural polynucleotide encoding the RrgA protein of *Streptococcus pneumoniae* or one of the homologues thereof. On the contrary, the polynucleotide according to the invention has been isolated and optionally purified, its environment has, consequently, been modified. The polynucleotide according to the invention may also be obtained by genetic recombination or by chemical synthesis.

The conditions of high stringency correspond to conditions of temperature and ionic force that make it possible to maintain a hybridization between two complementary nucleotide sequences. Those skilled in the art will know how to determine the most suitable conditions of high stringency particularly as a function of the size of the nucleotide sequences and by referring to the teaching of Sambrook et al. (Molecular cloning, 1989, Noland C. ed., New York: Cold Spring Harbor Laboratory Press).

"Polynucleotide" is taken to mean, within the scope of the present invention, a nucleic acid, a nucleic sequence, a nucleic acid sequence, an oligonucleotide, a polynucleotide sequence, a nucleotide sequence, a single stranded DNA, a double stranded DNA or an RNA. A polynucleotide according to the present invention may comprise natural nucleotides and non-natural nucleotides.

The polynucleotide according to the present invention comprises at least one nucleotide sequence having at least 40%, at least 45%, at least 50%, at least 55%, at least 60%, at least 65%, at least 70%, at least 75%, at least 80%, at least 85%, at least 90%, at least 95% and/or at least 99% of identity with one of the nucleotide sequences hereafter or one of the complementary sequences thereof:

```
                    (SEQ ID NO: 1 in the appended listing of
                                                  sequences)
CAGTATCCACAAACAGGGACTTATCCAGATGTTCAAACACCTTATCAGAT

TATTAAGGTAGATGGTTCGGAAAAAAACGGACAGCACAAGGCGTTGAATC

CGAATCCATATGAACGTGTGATTCCAGAAGGTACACTTTCAAAGAGAATT

TATCAAGTGAATAATTTGGATGATAACCAATATGGAATCGAATTGACGGT

TAGTGGGAAAACAGTGTATGAACAA
or

                    (SEQ ID NO: 3 in the appended listing of
                                                  sequences)
ATTGAGAATGGTACGATTACAGATCCGATGGGTGAGTTAATTGATTTGCA

ATTGGGCACAGATGGAAGATTTGATCCAGCAGATTACACTTTAACTGCAA

ACGATGGTAGTCGCTTGGAGAATGGACAAGCTGTAGGTGGTCCACAAAAT

GATGGTGGTTTGTTAAAAAATGCAAAAGTGCTCTATGATACGACTGAGAA

AAGGATTCGTGTAACAGGTCTGTACCTTGGAACGGATGAAAAAGTTACGT

TGACCTACAATGTTCGTTTGAATGATGAGTTTGTAAGCAATAAATTTTAT

GATACCAATGGTCGAACAACCTTACATCCTAAGGAAGTAGAACAGAACAC

AGTGCGCGACTTCCCGATTCCTAAGATTCGTGATCGTGAT.
```

It is clear that the polynucleotide according to the invention also covers the sequences encoding the fragments of the Jo and In peptides envisaged previously, the sequences having at least 40%, at least 45%, at least 50%, at least 55%, at least 60%, at least 65%, at least 70%, at least 75%, at least 80%, at least 85%, at least 90%, at least 95% and/or at least 99% of identity with the sequences encoding said fragments and the complementary sequences of such sequences. From the sequences of fragments envisaged and the nucleotide sequence encoding the Jo and In peptides, it is easy for those skilled in the art to identify the nucleotide sequence encoding a particular fragment.

It is also clear that the polynucleotide according to the invention also covers the sequences encoding the derivatives of the Jo and In peptides envisaged previously, the sequences having at least 40%, at least 45%, at least 50%, at least 55%, at least 60%, at least 65%, at least 70%, at least 75%, at least 80%, at least 85%, at least 90%, at least 95% and/or at least 99% of identity with the sequences encoding said derivatives and the complementary sequences of such sequences. From the sequences of derivatives envisaged and the nucleotide sequence encoding the Jo and In peptides, it is easy for those skilled in the art to identify the nucleotide sequence encoding a particular derivative. A particular example of polynucleotides encoding such derivatives corresponds:

either, to the polynucleotide encoding the derivative of the Jo peptide, the amino acid sequence of which is the sequence SEQ ID NO: 6 in the appended sequence listing, said polynucleotide having the following nucleotide sequence:

(SEQ ID NO: 5 in the appended listing of sequences)
TCTGACCAGTATCCACAAACAGGGACTTATCCAGATGTTCAAACACCTTA

TCAGATTATTAAGGTAGATGGTTCGGAAAAAAACGGACAGCACAAGGCGT

TGAATCCGAATCCATATGAACGTGTGATTCCAGAAGGTACACTTTCAAAG

AGAATTTATCAAGTGAATAATTTGGATGATAACCAATATGGAATCGAATT

GACGGTTAGTGGGAAAACAGTGTATGAACAAAAAGAT or, to the polynucleotide encoding the derivative of the In peptide, the amino acid sequence of which is the sequence SEQ ID NO: 8 in the appended sequence listing, said polynucleotide having the following nucleotide sequence:

(SEQ ID NO: 7 in the appended listing of sequences)
ACTGAAAAGAAATCAATTGAGAATGGTACGATTACAGATCCGATGGGTGA

GTTAATTGATTTGCAATTGGGCACAGATGGAAGATTTGATCCAGCAGATT

ACACTTTAACTGCAAACGATGGTAGTCGCTTGGAGAATGGACAAGCTGTA

GGTGGTCCACAAAATGATGGTGGTTTGTTAAAAAATGCAAAAGTGCTCTA

TGATACGACTGAGAAAAGGATTCGTGTAACAGGTCTGTACCTTGGAACGG

ATGAAAAAGTTACGTTGACCTACAATGTTCGTTTGAATGATGAGTTTGTA

AGCAATAAATTTTATGATACCAATGGTCGAACAACCTTACATCCTAAGGA

AGTAGAACAGAACACAGTGCGCGACTTCCCGATTCCTAAGATTCGTGAT.

Advantageously, the polynucleotide according to the present invention is constituted of one of the nucleotide sequences hereafter or one of the complementary sequences thereof:

(SEQ ID NO: 1 in the appended listing of sequences)
CAGTATCCACAAACAGGGACTTATCCAGATGTTCAAACACCTTATCAGAT

TATTAAGGTAGATGGTTCGGAAAAAAACGGACAGCACAAGGCGTTGAATC

CGAATCCATATGAACGTGTGATTCCAGAAGGTACACTTTCAAAGAGAATT

TATCAAGTGAATAATTTGGATGATAACCAATATGGAATCGAATTGACGGT

TAGTGGGAAAACAGTGTATGAACAA, (SEQ ID NO: 3 in the appended listing of sequences)
ATTGAGAATGGTACGATTACAGATCCGATGGGTGAGTTAATTGATTTGCA

ATTGGGCACAGATGGAAGATTTGATCCAGCAGATTACACTTTAACTGCAA

ACGATGGTAGTCGCTTGGAGAATGGACAAGCTGTAGGTGGTCCACAAAAT

GATGGTGGTTTGTTAAAAAATGCAAAAGTGCTCTATGATACGACTGAGAA

AAGGATTCGTGTAACAGGTCTGTACCTTGGAACGGATGAAAAAGTTACGT

TGACCTACAATGTTCGTTTGAATGATGAGTTTGTAAGCAATAAATTTTAT

GATACCAATGGTCGAACAACCTTACATCCTAAGGAAGTAGAACAGAACAC

AGTGCGCGACTTCCCGATTCCTAAGATTCGTGATCGTGAT, (SEQ ID NO: 5 in the appended listing of sequences)
TCTGACCAGTATCCACAAACAGGGACTTATCCAGATGTTCAAACACCTTA

TCAGATTATTAAGGTAGATGGTTCGGAAAAAAACGGACAGCACAAGGCGT

-continued

TGAATCCGAATCCATATGAACGTGTGATTCCAGAAGGTACACTTTCAAAG

AGAATTTATCAAGTGAATAATTTGGATGATAACCAATATGGAATCGAATT

GACGGTTAGTGGGAAAACAGTGTATGAACAAAAAGAT
or (SEQ ID NO: 7 in the appended listing of sequences)
ACTGAAAAGAAATCAATTGAGAATGGTACGATTACAGATCCGATGGGTGA

GTTAATTGATTTGCAATTGGGCACAGATGGAAGATTTGATCCAGCAGATT

ACACTTTAACTGCAAACGATGGTAGTCGCTTGGAGAATGGACAAGCTGTA

GGTGGTCCACAAAATGATGGTGGTTTGTTAAAAAATGCAAAAGTGCTCTA

TGATACGACTGAGAAAAGGATTCGTGTAACAGGTCTGTACCTTGGAACGG

ATGAAAAAGTTACGTTGACCTACAATGTTCGTTTGAATGATGAGTTTGTA

AGCAATAAATTTTATGATACCAATGGTCGAACAACCTTACATCCTAAGGA

AGTAGAACAGAACACAGTGCGCGACTTCCCGATTCCTAAGATTCGTGAT.

The present invention also relates to a cloning and/or expression vector containing at least one polynucleotide according to the present invention. Such a vector is particularly useful for transforming a host organism and expressing, therein, a peptide according to the present invention.

The vector according to the present invention further comprises one (or more) element(s) that enable the expression of the polynucleotide according to the present invention and/or the secretion of the product resulting from the translation of the polynucleotide according to the present invention. Among these elements may be cited a constitutive or inducible promoter, an initiation signal of the transcription or a termination signal of the transcription, a sequence for translation initiation or a translation termination signal.

Advantageously, the vector according to the present invention comprises, operably linked, a promoter, a polynucleotide of the invention and a terminator element. "Operably linked" is taken to mean, according to the invention, elements joined together such that the functioning of one of the elements is affected by that of another. As an example, a promoter is operably linked to an encoding sequence when it is capable of affecting the expression thereof. The regulating elements of the transcription, of the translation and of the maturation of the peptides that the vector may comprise are known to those skilled in the art and the latter is capable of choosing them as a function of the host organism in which the expression or the cloning need to be carried out.

The vector according to the present invention is advantageously selected from a plasmid, a cosmid, a bacteriophage and a virus such as a baculovirus. In particular, the vector of the invention is an autonomous replication vector comprising elements enabling its maintaining and its replication in the host organism as a replication origin. Moreover, the vector may comprise elements enabling its selection in the host organism such as, for example, a gene of resistance to an antibiotic or a selection gene that assures the complementation with the respective gene deleted at the level of the genome of the host organism. Such cloning and/or expression vectors are well known to those skilled in the art and are widely described in the literature.

The invention also relates to a host organism transformed by or comprising a polynucleotide according to the present invention or a vector according to the present invention.

"Host organism" is taken to mean any uni- or pluricellular, lower or higher, organism in which a polynucleotide of the invention is introduced for the production of a peptide according to the present invention.

Those skilled in the art know different methods for introducing in an efficient manner a polynucleotide into a host organism and to do so, in order that, in the host organism, the peptide encoded by said polynucleotide is produced. As an example and in a non-exhaustive manner, this method may be an electroporation, a lipofection, a biological transformation of a plant using *Agrobacterium tumefasciens*, a thermal shock or a chemical method.

Advantageously, the host organism is a micro-organism such as a yeast, a bacterium or a fungus. The transformation of such micro-organisms makes it possible to produce the peptide of the invention at semi-industrial or industrial scale.

In a variant, the host organism is an animal cell such as a mammal cell, a plant cell, an insect cell, an animal with the exception of a human, or a plant.

Such host organisms can be used to produce a peptide according to the present invention. In fact, a method for producing a peptide according to the present invention comprises the steps consisting in:

a) cultivating a host organism according to the present invention and particularly a unicellular host organism in a culture medium and in appropriate conditions;

b) recovering said peptide from the culture medium of said cultivated host organism or from said cultivated host organism.

The present invention relates to an element marked by at least one peptide according to the invention and as defined previously.

"Element" is taken to mean a compound or a solid support to which a peptide according to the invention is attached, bound, fixed and/or associated or with which a peptide according to the invention is complexed and/or conjugated.

In a 1$^{st}$ embodiment, the element marked according to the present invention may be a solid support on the surface of which one (or more) peptide(s) according to the invention is(are) immobilized.

In a variant of the invention, the solid support or at least the surface of said solid support where the peptide(s) according to the invention is(are) immobilized is particularly a solid support or an inorganic surface. In fact, a solid support may be envisaged of which only the surface is made of a particular inorganic material, the remainder of the support being made of another inorganic material or made of an organic material. Advantageously, the solid support or the surface of said solid support is made of an inorganic material selected from the group consisting of glasses, quartzes, ceramics (for example, of oxide type), metals (for example, aluminium, chromium, copper, zinc, silver, nickel, tin or gold), metalloids (for example, silicon or oxidised silicon) and mixtures thereof.

In another variant of the invention, the solid support or at least the surface of said solid support where the peptide(s) according to the invention is(are) immobilized is made of an organic material such as a polymer such as agarose or a resin including nylon, polyethylene glycol, polycarbonates, polyfluoropolymers or composites. It is also possible to envisage a solid support of which only the surface is made of a particular organic material, the remainder of the support being made of another organic material or an inorganic material.

Said solid support may come in various forms of variable size. As examples and in a non-exhaustive manner, it can come in the form of sheets, microplates particularly 12, 24 or 96 well microplates, microplatelets, particles, beads, microbeads, fibres, felts, tubes such as haemolysis tubes or microchannels of capillary type, columns or microcolumns such as SPIN™ columns, supports used for biosensors or biochips. These different types of support may have sizes varying from several hundreds of micrometers to several centimeters.

Advantageously, the solid support has a surface bearing functional groups thanks to which the peptide(s) according to the invention is(are) capable of immobilizing themselves. In a particular manner, said functional groups are selected from carboxylic groups, radical entities, alcohol, amine, amide, epoxy or thiol functions. This functionalization may be intrinsic to the nature of the material on the surface of the solid support implemented. In an alternative manner, this functionalization may be obtained by cleaning of said surface through the intermediary of at least one solvent, detergent, radiation or oxygen plasma or any other method enabling the formation of functional groups as defined previously.

In a 1$^{st}$ variant of the functionalized support of the present invention, the peptide according to the invention may be immobilized in a direct manner on the surface of the solid support, functionalized or not. A solid support "coated" with a Jo or In peptide according to the invention is an example of direct immobilization. In this variant, the peptide according to the invention is advantageously bound to the surface of the solid support functionalized or not by means of a covalent bond. Thus, this covalent bond bounds an atom of the surface of the solid support, functionalized or not, to an atom of the peptide according to the invention.

In a 2$^{nd}$ variant of the functionalized support of the present invention, the peptide according to the invention may be indirectly immobilized on the surface of the solid support, functionalized or not. This indirect immobilization involves a spacer arm (or junction agent) bound, on the one hand, to the solid support and, on the other hand, to the peptide according to the invention. Those skilled in the art know different examples of such spacer arms. In a non-exhaustive manner may be cited, as spacer arms capable of being implemented within the scope of the present invention, 1,6 diaminohexane, 6-aminohexanoic acid, a succinimide group, an epoxide, UDP-glucuronic acid, linear or branched alkyl chains of 1 to 20 carbon atoms, pyrrole, silanes, polyethylene glycol, glutaraldehyde, etc.

Whether the immobilization on the solid support is direct or indirect, the peptide according to the invention may be immobilized via the N-terminal end thereof, via the C-terminal end thereof or via the side chain of one of the amino acids constituting it. In all cases, the only constraint is that the bond with its partner (i.e. Jo peptide, In peptide, derivatives or fragments thereof) is not affected.

The bonds implemented during a direct or indirect immobilization can be any bonds known to those skilled in the art and particularly covalent bonds, ionic bonds, hydrogen bonds, an adsorption, etc.

In a 2$^{nd}$ embodiment, the element marked according to the present invention may be a compound conjugated with at least one peptide according to the invention and as defined previously.

The compound as implemented in the present invention is particularly a natural or synthetic molecule such as a biological or biologically active molecule, a monomer, an easily detectable compound or a cytotoxic compound.

"Biological or biologically active molecules" are natural or synthetic molecules, advantageously selected from epitopes; antigens; peptides; oligopeptides; proteins such as an enzyme; antibodies and fragments of antibodies; cellular or membrane receptors; polysaccharides; cells or cellular parts such as organites or cellular membranes and nucleic molecules.

Among biological or biologically active molecules, an oligopeptide advantageously used within the scope of the present invention results from the fusion of at least two peptides according to the invention, identical or different. Such an oligopeptide meets the formula (I) hereafter:

$$[(Jo)_m\text{-}(In)_n]_r \qquad (I)$$

wherein:

m represents a whole number comprised between 0 and 50, n represents a whole number comprised between 0 and 50 and r represents a whole number comprised between 1 and 50, when m is equal to 0, n represents a whole number comprised between 1 and 50;

when n is equal to 0, m represents a whole number comprised between 1 and 50;

when r represents a whole number greater than or equal to 2, for each repetition i with i representing a whole number comprised between 1 and (r−1), mi representing the value m in the repetition i is identical or different to m(i+1) representing the value m in the repetition i+1 and ni representing the value n in the repetition i is identical or different to n(i+1) representing the value n in the repetition i+1.

"Nucleic molecules" is taken to mean a single or double stranded DNA, RNA, an iRNA, an aptamer, a PNA (Peptide Nucleic Acid) or an LNA (Locked Nucleic Acid).

"Easily detectable compound" is taken to mean, within the scope of the present invention, a compound that may be detected by implementation of an appropriate detection technique, advantageously non-invasive, such as microscopy, scintigraphy and magnetic resonance imaging (MRI). An element according to the invention comprising such an easily detectable compound is particularly suited to the field of imaging or diagnostics. It makes it possible in particular to identify and localize sites at the level of which the Jo peptide (or the In peptide) is present, said element consisting of an easily detectable compound conjugated with the In peptide (or the Jo peptide). In this application, the presence of the Jo peptide (or of the In peptide) at the level of a particular site may be the result of the expression at the level of this site of a fusion protein corresponding to a particular protein such as a membrane receptor, fused directly or indirectly to the Jo peptide (or to the In peptide).

As particular examples of easily detectable compounds may be cited:

- an enzyme or a molecule capable of generating a detectable and optionally quantifiable signal in particular conditions such as during the bringing into presence of a suitable substrate, such as biotin, digoxygenin, 5-bromodeoxyuridine, an alkaline phosphatase, a peroxidase, an acetylcholine esterase (AChE), a glucose amylase and a lysozyme; or
- a fluorescent, chemofluorescent or bioluminescent marker such as fluorescein and derivatives thereof, rhodamine and derivatives thereof, GFP (Green Fluorescent Protein) and derivatives thereof, and umbelliferone; luminol; luciferase and luciferin;
- a radioactive marker, which can be introduced into the peptide sequence of the peptide according to the invention or which can be borne by a compound separate from the peptide according to the invention and conjugated to the latter. In the case of the 1st alternative (i.e. radioactive marker introduced into the peptide according to the invention), this introduction may take place during the synthesis of the peptide according to the invention using one or more marked amino acids. In a variant, this introduction may take place following this synthesis by fixing the radioactive marker on residues of the peptide sequence of the synthesized peptide according to the invention. For example, yttrium-90 may be fixed via a lysine residue. In the 2nd alternative, the radioactive marker may be indirectly fixed to the peptide according to the invention by known means. For example, EDTA or another chelating agent may be fixed to the peptide according to the invention and used to fix indium-111.

"Cytotoxic compound" is taken to mean, within the scope of the present invention, a compound directly or indirectly toxic. "Directly cytotoxic" is taken to mean a compound that is in itself cytotoxic. "Indirectly cytotoxic" is taken to mean a compound which, although non-cytotoxic as such, may induce a cytotoxicity, for example by its action on another molecule or by a supplementary action on it.

As particular examples of cytotoxic compounds may be cited:

- a cytotoxic chemotherapeutic agent, the activity of which may optionally be increased under irradiation, such as alkylating agents such as mechlorethamine or chlorambucile; methotrexate; 5-fluoro-uracile; vinblastine; gemcitabine; fludarabine; nicotinamide; doxorubicin; mitomycin; L-asparaginase; cisplatin; taxol and analogues/derivatives thereof;
- a cytotoxic (poly)peptide group such as ricin, abrin, *Pseudomonas* exotoxin, TNFα and interleukin 2;
- an indirectly cytotoxic chemotherapeutic agent, also known as pro-drug, which is not or not very cytotoxic as such but is capable of giving, particularly following an enzymatic reaction or an irradiation, a cytotoxic substance (or drug) particularly as defined previously. Examples of pro-drugs are particularly methotrexate-alanine; mitomycin phosphate, 5-fluorocytosine; photofrin and capecitabine;
- an indirectly cytotoxic (poly)peptide group which has an enzymatic activity and can convert a relatively non-toxic pro-drug particularly as defined previously into a cytotoxic substance. Examples of pro-drugs are particularly a peptidase such as a carboxypeptidase, an aminopeptidase or an endopeptidase; a phosphatase; a sulphatase; an amidase; a kinase; a glycosidase; a deaminase; a reductase; and an oxidase;
- a nucleic acid molecule that is directly or indirectly cytotoxic such as an antisense oligonucleotide or an aptamer.

In this 2nd embodiment, the element marked according to the present invention may be a compound conjugated by a single peptide as defined previously. The conjugation with the peptide may be direct or indirect by implementing a spacer arm as defined previously for the immobilization of a peptide of the invention on a solid support.

In a variant, the element marked according to the present invention may be a compound conjugated by two peptides, identical or different, as defined previously. Each of the peptides may be, independently of each other, directly or indirectly bound to the compound.

In this variant, the following cases are possible:

- a compound conjugated directly with the Jo peptide, a derivative or a fragment thereof and directly with the In peptide, a derivative or a fragment thereof;
- a compound conjugated indirectly with the Jo peptide, a derivative or a fragment thereof and directly with the In peptide, a derivative or a fragment thereof;

- a compound conjugated directly with the Jo peptide, a derivative or a fragment thereof and indirectly with the In peptide, a derivative or a fragment thereof;
- a compound conjugated indirectly with the Jo peptide, a derivative or a fragment thereof and indirectly with the In peptide, a derivative or a fragment thereof;
- a compound conjugated directly with a 1st Jo peptide, a derivative or a fragment thereof and directly with a 2nd Jo peptide, a derivative or a fragment thereof;
- a compound conjugated directly with a 1st Jo peptide, a derivative or a fragment thereof and indirectly with a 2nd Jo peptide, a derivative or a fragment thereof;
- a compound conjugated indirectly with a 1st Jo peptide, a derivative or a fragment thereof and indirectly with a 2nd Jo peptide, a derivative or a fragment thereof;
- a compound conjugated directly with a 1st In peptide, a derivative or a fragment thereof and directly with a 2nd In peptide, a derivative or a fragment thereof;
- a compound conjugated directly with a 1st In peptide, a derivative or a fragment thereof and indirectly with a 2nd In peptide, a derivative or a fragment thereof;
- a compound conjugated indirectly with a 1st In peptide, a derivative or a fragment thereof and indirectly with a 2nd In peptide, a derivative or a fragment thereof.

Whether the conjugation with the compound is direct or indirect, the peptide(s) according to the invention may be conjugated via the N-terminal end(s) thereof, via the C-terminal end(s) thereof or via the side chain of one of the amino acids constituting it. In all cases, the only constraint is that the bond with its partner (i.e. Jo peptide, In peptide, fragments thereof or derivatives thereof) is not affected.

The bonds implemented during direct or indirect conjugation can be any bonds known to those skilled in the art and particularly covalent bonds, ionic bonds, hydrogen bonds, an adsorption, etc.

In a particular embodiment, a peptide according to the invention may be conjugated via the N-terminal end thereof, directly or indirectly, to a 1st compound as defined previously and via the C-terminal end thereof, directly or indirectly, to a 2nd compound as defined previously, identical or different to the 1st compound.

Those skilled in the art know different techniques making it possible to conjugate such compounds to one (or more) peptide(s) according to the present invention once the latter obtained or produced or prior to its being obtained.

These techniques enable a covalent coupling between a peptide according to the invention and a compound by taking advantage of the particular chemical groups borne by the peptide according to the invention and by the compound. Among these particular chemical groups may be cited a thiol group, an ester group, an amino group, an acid group and any chemical element capable of being implemented in "click-chemistry".

In a variant and particularly when the compound is of peptide nature, this conjugation may consist in producing the compound conjugated according to the invention in the form of a fusion compound by genetic recombination techniques, in which a polynucleotide comprises respective regions encoding the peptide according to the present invention and the compound, adjacent to each other, juxtaposed or separated by a region encoding a spacer arm such as a peptide linker which does not destroy the desired properties of the final fusion compound.

Similarly, when the compound according to the invention is conjugated by two peptides according to the invention and when said compound is of peptide nature, it is also possible to envisage a production by means of a polynucleotide comprising a region encoding the 1st peptide according to the invention then a region encoding the compound and finally a region encoding the 2nd peptide according to the invention, each of the regions which can be juxtaposed with the region that follows it or separated from the latter by a region encoding a spacer arm of the peptide linker type.

Likewise, when the peptide according to the invention is conjugated by two compounds and when said compounds are of peptide nature, a production may also be envisaged by means of a polynucleotide comprising a region encoding the 1st compound then a region encoding the peptide according to the invention and finally a region encoding the 2nd compound, each of the regions which can be juxtaposed with the region that follows it or separated from the latter by a region encoding a spacer arm of the peptide linker type.

If two spacer arms are implemented on a same conjugate, the latter can be identical or different.

Whatever the technique used to conjugate a peptide according to the present invention with a compound, the only constraint to respect within the scope of this conjugation is that the conjugated peptide i.e. the Jo peptide (or the In peptide) conserves its bonding specificity with the other peptide according to the invention i.e. the In peptide (or the Jo peptide).

The two peptides according to the present invention via their capacity to form a covalent and irreversible complex play the role of molecular glue, useful for assembling two surfaces (FIG. 1A), two solid supports, two compounds (FIGS. 1B, 1C and 1D), a surface and a solid support, a surface and a compound or a solid support and a compound, said solid support, said surface and said compound being as defined previously i.e. a solid support, a surface and a compound functionalized, directly or indirectly, with at least one peptide according to the invention.

The present invention relates to the use of a solid support according to the present invention and a compound conjugated to at least one peptide according to the invention for purifying said compound or for preparing a biochip or a biosensor.

In fact, the compound may be a compound of interest which can be purified using a solid support according to the present invention. In this case, the compound of interest is advantageously conjugated to a single peptide according to the invention. This method for purifying a compound of interest comprises the steps consisting in:

- conjugating said compound of interest with a peptide according to the present invention (i.e. with either the Jo peptide, a derivative or a fragment thereof, or of the In peptide, a derivative or a fragment thereof);
- placing the compound of interest thereby conjugated with a solid support on which is immobilized at least one other peptide according to the present invention (i.e. either the In peptide, a derivative or a fragment thereof, if the compound is conjugated with the Jo peptide, a derivative or a fragment thereof; or the Jo peptide, a derivative or a fragment thereof, if the compound is conjugated with the In peptide, a derivative or a fragment thereof). In this purification method, the solid support implemented is advantageously a purification column, a resin or a matrix normally used in affinity chromatography.

For such an application, it may be advantageous to use a compound of interest indirectly conjugated to a peptide according to the invention. In fact, a spacer arm between the compound of interest and the peptide according to the invention and particularly a peptide spacer arm capable of being enzymatically cleaved makes it possible to recover the compound of interest, following the action of the cleaving enzyme such as a protease.

Thus, the present invention relates to a method for purifying a compound, comprising the steps consisting in:

conjugating indirectly said compound with one of the two peptides according to the present invention (i.e. with either the Jo peptide, a derivative or a fragment thereof, or the In peptide, a derivative or a fragment thereof), a cleavable spacer arm separating said compound and said peptide;

preparing a solid support on the surface of which the other of the two peptides according to the present invention (i.e. either the In peptide, a derivative or a fragment thereof, if the compound is conjugated with the Jo peptide, a derivative or a fragment thereof; or the Jo peptide, a derivative or a fragment thereof, if the compound is conjugated with the In peptide, a derivative or a fragment thereof) is immobilized;

placing the compound thereby conjugated in the presence of the support thereby prepared, whereby the conjugated compound is immobilized on the solid support, this immobilization involving an isopeptide bond;

subjecting the compound thereby immobilized to conditions enabling the cleavage thereof; and recovering the purified cleaved compound.

The present invention also relates to a purification kit comprising:

a solid support on the surface of which one of the two peptides according to the present invention (i.e. either the In peptide, a derivative or a fragment thereof; or the Jo peptide, a derivative or a fragment thereof) is immobilized;

an element selected from a peptide corresponding to the other peptide according to the invention; a polynucleotide as defined previously encoding said peptide or an expression and/or cloning vector as defined previously containing said polynucleotide.

It is clear that the other element of the purification kit according to the invention is to associate, conjugate or to fuse with the compound to be purified or with a nucleotide sequence encoding such a compound.

"The other peptide" is taken to mean the In peptide, a derivative or a fragment thereof, if the Jo peptide, a derivative or a fragment thereof is immobilized on the support; or the Jo peptide, a derivative or a fragment thereof, if the In peptide, a derivative or a fragment thereof is immobilized on the support.

Similarly, the present invention may be used for the preparation of biochips or biosensors. This preparation may have different embodiments:

preparing a solid support on which is immobilized at least one peptide member of the heterodimer according to the present invention (i.e. either the Jo peptide, a derivative or a fragment thereof; or the In peptide, a derivative or a fragment thereof) then depositing a compound conjugated to at least one peptide, other member of the heterodimer according to the present invention (i.e. either the In peptide, a derivative or a fragment thereof, if, on the solid support, the immobilized peptide is the Jo peptide, a derivative or a fragment thereof; or the Jo peptide, a derivative or a fragment thereof, if, on the solid support, the immobilized peptide is the In peptide, a derivative or a fragment thereof) on the total surface of the support; or depositing this conjugated compound thanks to a micro or nano-fluidic system in a direct or sequential manner in the form of droplets: or soaking the solid support on which is immobilized at least one peptide according to the present invention in the solution containing said conjugated compound.

Within the scope of the preparation of said biochip or of said biosensor, the compound conjugated to the peptide according to the invention may be any compound normally used in this type of application. More particularly, said compound is a biological or biologically active molecule as defined previously.

In addition, said compound may be conjugated by one or two peptides according to the present invention. In fact, it may be envisaged to obtain a biochip or a biosensor having, on the surface, two compounds bound to each other. A particular example of such a variant consists in using a solid support on which is immobilized the Jo peptide, a derivative or a fragment thereof and placing it in contact with a solution containing a compound A marked by the Jo peptide, a derivative or a fragment thereof and by the In peptide, a derivative or a fragment thereof and a compound B marked by the In peptide, a derivative or a fragment thereof, said solution containing, due to the remarkable interaction properties between Jo and In, a compound resulting from the bonding of the compound A with the compound B. In other words, the complex AB is formed prior to the placing in contact with the solid support. In a variant, it may be envisaged to apply on the solid support a $1^{st}$ solution containing the compound A, then a $2^{nd}$ solution containing the compound B.

The present invention also relates to the biochip or the biosensor capable of being prepared according to the method of preparation of the present invention i.e. by using a solid support and a compound conjugated according to the present invention. In fact, said biochip and said biosensor can be distinguished from the biochips and biosensors of the prior art by the presence between the solid support and the compound immobilized on its surface of the Jo/In heterodimer.

The use of the present invention for purifying compounds of interest or for preparing biochips and biosensors has numerous advantages. It does not require chemical modification of the compound of interest, it enables the control of the orientation of the compound of interest on the surface of the solid support and makes it possible that the compound of interest is stably bound to this surface.

Moreover, when the compound of interest is of peptide nature and when its conjugation to at least one peptide according to the invention is obtained by means of a fusion protein, the preparation of biochips or biosensors may be carried out on non-purified lysates containing the compound of interest of peptide nature.

In this schematisation of FIG. 2, the Jo peptide (Jo) is bound by chemical reaction to the surface of a solid support and the compound according to the invention is a protein of interest conjugated to the In peptide (In) but separated therefrom by a spacer arm having the specific cut-off site of cysteine protease TEV (TEV). Once the compound according to the invention is placed in contact with the solid support according to the invention, the complex obtained may be subject to the action of cysteine protease TEV, thereby releasing the protein of interest (case of purification). In a variant, the complex constitutes a biosensor or a biochip for studying interactions involving the protein of interest.

The present invention also relates to a compound according to the present invention i.e. a compound conjugated to a peptide according to the present invention for use in medicine or for diagnostics.

The present invention also comprises a diagnostic or treatment kit comprising two compounds according to the present invention. More particularly, the diagnostic or treatment kit according to the present invention comprises:

in a $1^{st}$ compartment, a $1^{st}$ compound capable of recognizing or targeting a pathologic site and conjugated with one of the two peptides according to the invention or a precursor of such a compound; and in a $2^{nd}$ compartment, a $2^{nd}$ easily detectable (for the diagnostic kit) or cytotoxic (for the treatment) compound marked by the other peptide according to the present invention.

The kit according to the present invention may thus comprise:

a $1^{st}$ compound capable of recognizing or targeting a pathologic site and conjugated with the Jo peptide, a derivative or a fragment thereof or a precursor of such a compound and a $2^{nd}$ easily detectable compound marked by the In peptide, a derivative or a fragment thereof; or a $1^{st}$ compound capable of recognizing or targeting a pathologic site and conjugated with the Jo peptide, a derivative or a fragment thereof or a precursor of such a compound and a $2^{nd}$ cytotoxic compound marked by the In peptide, a derivative or a fragment thereof; or a $1^{st}$ compound capable of recognizing or targeting a pathologic site and conjugated with the In peptide, a derivative or a fragment thereof or a precursor of such a compound and a $2^{nd}$ easily detectable compound marked by the Jo peptide, a derivative or a fragment thereof; or a $1^{st}$ compound capable of recognizing or targeting a pathologic site and conjugated with the In peptide, a derivative or a fragment thereof or a precursor of such a compound and a $2^{nd}$ cytotoxic compound marked by the Jo peptide, a derivative or a fragment thereof.

A compound capable of recognizing or targeting a pathologic site may be an antibody or a fragment of antibodies capable of recognizing a marker present on the surface of pathological cells such as cancerous cells. Said compound may also be a ligand of such a marker present on the surface of pathological cells. In a further variant, said compound may be a membrane protein capable of being expressed in the pathological cells. In fact, the precursor of said compound may be a nucleic acid encoding a fusion protein corresponding to this protein and to the peptide according to the invention, to which it is fused.

The compounds present in the two compartments of the kit according to the invention can be administered in a simultaneous manner or one after the other. The kits according to the invention can be used in vivo as well as in vitro and particularly on biological samples derived beforehand from a living system, human or animal.

The present invention further relates to the use of a compound according to the present invention and particularly a compound conjugated with a single peptide according to the invention to crystallize said compound.

This use is based on the property of the Jo and In peptides associated together to crystallize in robust conditions and making it possible to obtain crystals with a good diffraction quality, as explained previously. Such a property makes it possible to envisage forming crystals from compounds normally difficult to crystallize such as proteins and particularly membrane proteins.

The method for crystallizing a compound according to the present invention consists in:

conjugating said compound with one of the two peptides according to the present invention (i.e. with either the Jo peptide, a derivative or a fragment thereof, or the In peptide, a derivative or a fragment thereof);

placing the compound thereby conjugated in the presence of the other peptide according to the present invention (i.e. either the In peptide, a derivative or a fragment thereof, if the compound is conjugated with the Jo peptide, a derivative or a fragment thereof; or the Jo peptide, a derivative or a fragment thereof, if the compound is conjugated with the In peptide, a derivative or a fragment thereof);

subjecting the compound thereby obtained to conditions enabling the crystallization thereof.

The compound that is obtained during the $2^{nd}$ step corresponds to a compound conjugated with one of the two peptides according to the invention, a fragment or a derivative thereof and having the other peptide according to the invention, a fragment or a derivative thereof associated with the $1^{st}$ peptide via an isopeptide bond.

When the compound according to the invention is conjugated to a peptide according to the invention or to two peptides according to the invention, circular structures can be obtained. The present invention thus relates to a circular structure comprising at least one compound as defined previously.

In fact, when the compound according to the invention is a compound of oligonucleotide type of formula (I) directly or indirectly conjugated to a peptide according to the invention, the latter may have an intra-molecular circularization.

An intra-molecular circularization may also be obtained within the scope of a compound of large or flexible protein type, conjugated at the N-terminal end thereof, directly or indirectly, with one of the two peptides according to the invention and at the C-terminal end thereof, directly or indirectly, with the other peptide according to the invention. FIG. 3A is a representation of an intra-molecular circularization.

In a variant, when the compound according to the invention is conjugated at the N-terminal end thereof, directly or indirectly, with one of the two peptides according to the invention and at the C-terminal end thereof, directly or indirectly, with the other peptide according to the invention, an inter-molecular circularization may be obtained. This is particularly the case when the compound implemented does not have a sufficient length and/or due to too important steric hindrances. FIG. 3B is a representation of an inter-molecular circularization that implements two identical compounds according to the invention.

When the compound according to the invention is conjugated to a peptide according to the invention or to two peptides according to the invention, multimeric structures can be obtained.

The present invention thus relates to a multimeric structure comprising at least two and advantageously a plurality of compounds, identical or different, each compound being bound to at least one other compound by an isopeptide bond. The isopeptide bond involves, in fact, a Jo peptide, a derivative or a fragment thereof conjugated with one of the compounds and a In peptide, a derivative or a fragment thereof conjugated with another of the compounds.

All of the cases of compounds conjugated by two peptides according to the invention as defined previously and listed may be envisaged for this use, the only constraint being that a compound either conjugated by the Jo peptide, a derivative or a fragment thereof and another compound, identical to or different from the $1^{st}$, or conjugated by the In peptide, a derivative or a fragment thereof in order to obtain an isopeptide bond. The multimerization that is obtained by bringing into contact these different compounds is a multimerization by polymerization.

The multimeric structure thereby obtained may result in a reconstitution or in a coupling of functions, particularly when the compound(s) implemented are compounds of peptide nature, and propose multiple interaction sites. This structure makes it possible to increase the avidity of a given interaction.

As particular examples of such multimeric structures may be cited:

- a structure in which a single compound is implemented and the latter is an antigen;
- a structure in which several compounds are implemented and are different antigens; such a structure having a particular interest in the field of vaccination since it enables an optimized presentation of antigens;
- a structure in which several compounds are implemented and are different monomers; such a structure having a particular interest in the field of polymerization since it makes it possible to obtain new polymers which would not have been able to be obtained differently when monomers incapable of polymerizing together are used.

A multimerization can also be obtained by using compounds of oligopeptide type of formula (I) directly or indirectly conjugated to a single one of the peptides according to the invention. FIG. 4 is a representation of the multimeric structure being able to be obtained using a compound of formula (I) with m=0 and n=r=1 directly conjugated with the In peptide and a compound of formula (I) with m=5, n=0 and r=1 directly conjugated with the Jo peptide.

The circular and multimeric structures according to the invention can be used for preparing antibodies.

Other characteristics and advantages of the present invention will become even clearer to those skilled in the art on reading the examples below given in an illustrative and non-limiting manner, while referring to the appended figures.

BRIEF DESCRIPTION OF DRAWINGS

FIG. 14 presents the detection of the CK and Jo-B1CK-In proteins by Western blot by polyclonal antibodies directed against Jo-B1CK-In.

DETAILED DESCRIPTION OF PARTICULAR EMBODIMENTS

Figure 1A:
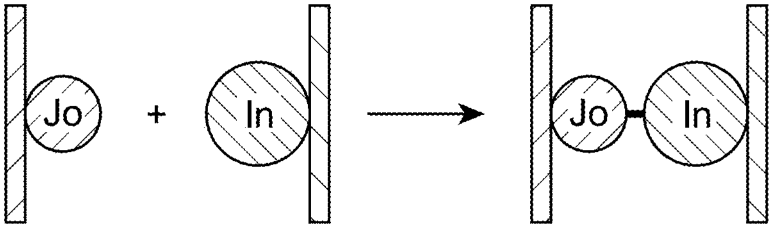
FIG. 1 shows the use of the peptides according to the invention as molecular glue for assembling two surfaces (FIG. 1A) or two compounds of protein type (FIGS. 1B, 1C and 1D).
FIG. 1B and FIG. 1C show two different complexes that could be obtained depending on whether the Jo peptide is fused to the C-terminal or N-terminal end of one of the proteins.
FIG. 1D is a representation of the complex obtained by using, on the one hand, a Jo peptide fused in N-terminal to a $1^{st}$ protein and in C-terminal to a $2^{nd}$ protein and, on the other hand, an In peptide fused in N-terminal to a $3^{rd}$ protein and in C-terminal to a $4^{th}$ protein.
Figure 1B:
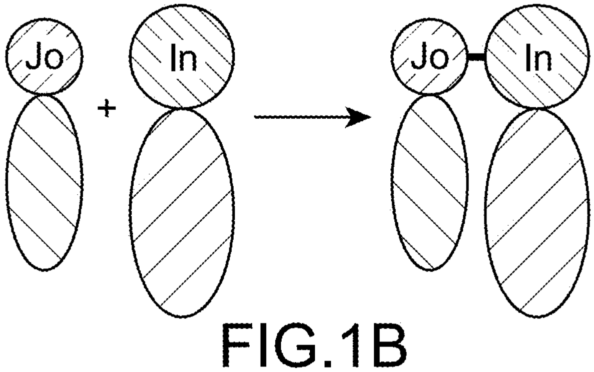
Figure 1C:
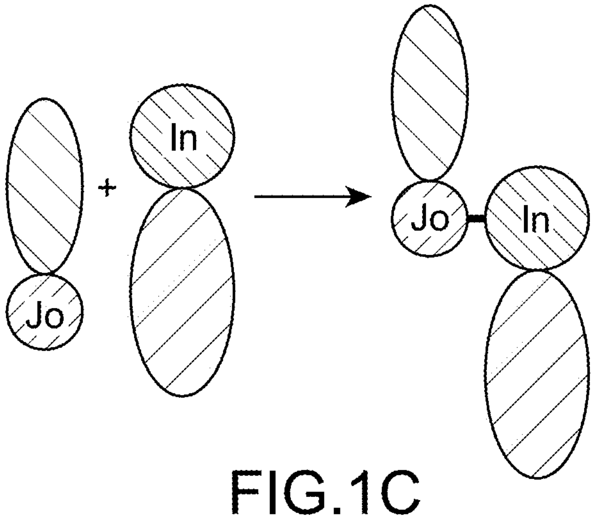
Figure 1D:
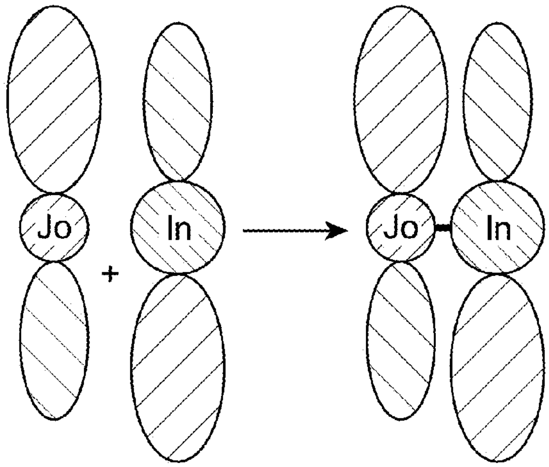
Figure 2:
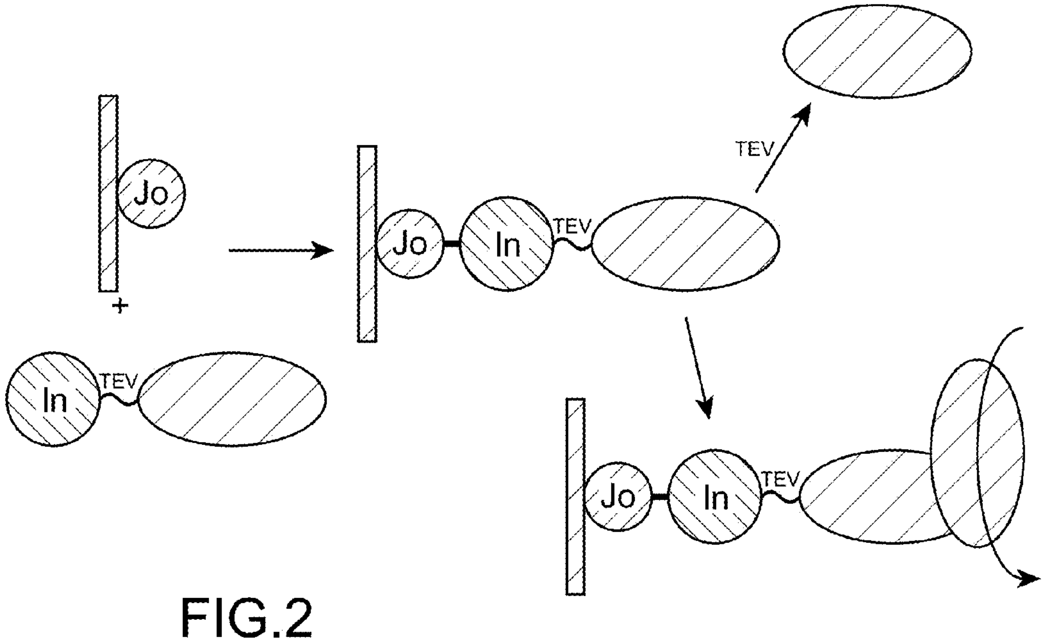
FIG. 2 is a schematisation of the use of the present invention for purifying a compound or for preparing a biochip or a biosensor, showing that the Jo peptide (Jo) is bound by chemical reaction to the surface of a solid support and the compound according to the invention is a protein of interest conjugated to the In peptide (In) but separated therefrom by a spacer arm having the specific cut-off site of cysteine protease TEV (TEV).
Figure 3A:
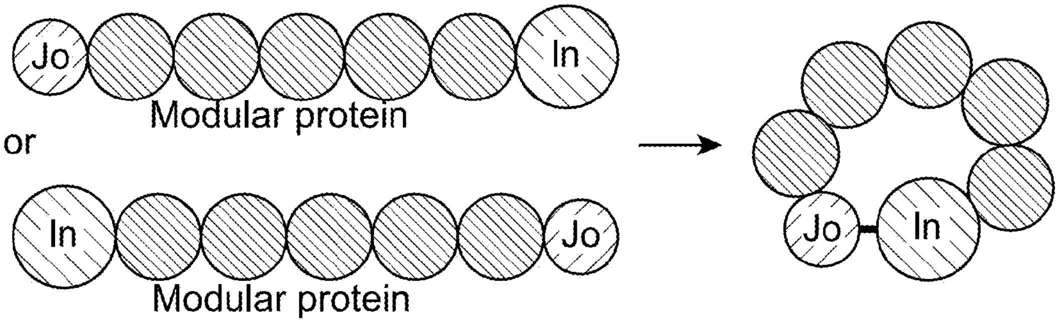
FIG. 3 presents circular structures that could be obtained with the peptides according to the invention via an intra-molecular (FIG. 3A) or inter-molecular (FIG. 3B) circularization.
Figure 3B:
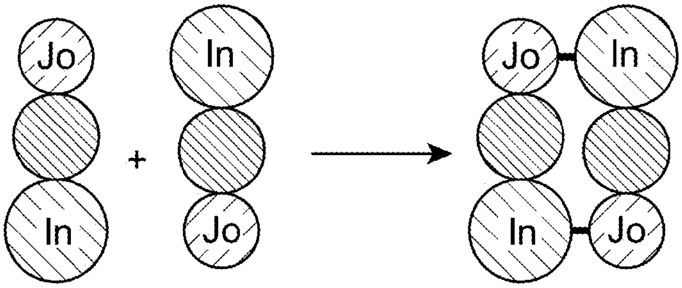
Figure 4:
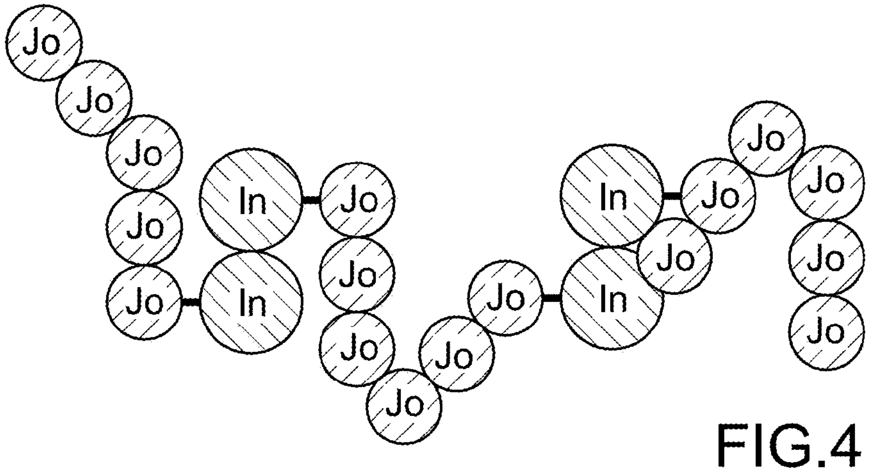
FIG. 4 presents a particular type of multimeric structure that could be obtained with the peptides according to the invention.

I. Production and Purification of the "JoIn" Complex.

I.1. Materials and Methods.

A. Sequences of Genes and Proteins of Derivatives of Jo and In.

Sequence Derived from Jo: Nucleotide Sequence (SEQ ID NO: 5 in the appended listing of sequences)

```
TCTGACCAGTATCCACAAACAGGGACTTATCCAGATGTTCAAACACCTTA
TCAGATTATTAAGGTAGATGGTTCGGAAAAAAACGGACAGCACAAGGCGT
TGAATCCGAATCCATATGAACGTGTGATTCCAGAAGGTACACTTTCAAAG
AGAATTTATCAAGTGAATAATTTGGATGATAACCAATATGGAATCGAATT
GACGGTTAGTGGGAAAACAGTGTATGAACAAAAAGAT
```

Sequence Derived from Jo: Amino Acid Sequence (SEQ ID NO: 6 in the appended listing of sequences)
SDQYPQTGTYPDVQTPYQIIKVDGSEKNGQHKALNPNPYERVIPEGTLSKR

IYQVNNLDDNQYGIELTVSGKTVYEQKD

Sequence Derived from In: Nucleotide Sequence (SEQ ID NO: 7 in the appended listing of sequences)
ACTGAAAAGAAATCAATTGAGAATGGTACGATTACAGATCCGATGGGTGA

GTTAATTGATTTGCAATTGGGCACAGATGGAAGATTTGATCCAGCAGATT

ACACTTTAACTGCAAACGATGGTAGTCGCTTGGAGAATGGACAAGCTGTA

GGTGGTCCACAAAATGATGGTGGTTTGTTAAAAAATGCAAAAGTGCTCTA

TGATACGACTGAGAAAAGGATTCGTGTAACAGGTCTGTACCTTGGAACGG

ATGAAAAAGTTACGTTGACCTACAATGTTCGTTTGAATGATGAGTTTGTA

AGCAATAAATTTTATGATACCAATGGTCGAACAACCTTACATCCTAAGGA

AGTAGAACAGAACACAGTGCGCGACTTCCCGATTCCTAAGATTCGTGAT

Sequence Derived from In: Amino Acid Sequence (SEQ ID NO: 8 in the appended listing of sequences)
TEKKSIENGTITDPMGELIDLQLGTDGRFDPADYTLTANDGSRLENG

QAVGGPQNDGGLLKNAKVLYDTTEKRIRVTGLYLGTDEKVTLTYNVR

LNDEFVSNKFYDTNGRTTLHPKEVEQNTVRDFPIPKIRD

B. Cloning of Genes Encoding for Derivatives of Jo and of In in Bicistronic Vectors.

The genes encoding for the sequences derived from Jo and of In were amplified by PCR from genomic DNA of the strain of *S. pneumoniae* TIGR4. The gene fragments encoding for derivatives of Jo and of In were cloned by restriction enzymes in the pETDuet vector (Novagen), respectively in MCSI and II: either in the same plasmid (co-expression of the Jo and In peptides) or in separate vectors enabling the expression of Jo and In in an independent manner; the cloning of the gene encoding for Jo in the MCSI of the pETDuet vector leads to the fusion in N-terminal of a 6×His label. The gene encoding for In in fusion with a 6×His label is cloned in the pACYCDuet vector in the MCSI site. The fusion of the Jo and In genes was carried out by directed mutagenesis (Stratagene).

C. Constructed Vectors.

| | |
|---|---|
| pETDuet-HisJoIn | co-expression of the derivatives of Jo (His tag in N-ter) and of In |
| pETDuet-HisJo | expression of a derivative of Jo (His tag in N-ter) |
| pETDuet-In | expression of a derivative of In |
| pACYCDuet-HisIn | expression of a derivative of In (His tag in N-ter) |
| pETDuet-FusJoIn | fusion of the derivatives of Jo (His tag in N-ter) and of In |

D. Production of Proteins and Complexes.

The strain of *E. coli* BL21(DE3)Star is transformed by the vectors constructed and indicated above. Each culture transformed with the pETDuet plasmid contains 100 μg/ml of ampicillin and with 34 μg/ml of chloramphenicol when the pACYCDuet plasmid is used. A pre-culture of 50 ml of LB medium is inoculated and incubated for 16 h at 37° C. under stirring then is used to inoculate 500 ml of LB medium. The bacterial culture takes place at 37° C. under stirring for 2 h then a solution of 0.5 mM final IPTG is added in order to induce the expression of the peptides derivatives of Jo and In.

In order to test the expression of the recombinant proteins, a volume of 5 μl of the resulting cultures is withdrawn, 5 μl of denaturing solution known as "Laemmli" buffered to pH 8.0 containing a detergent (SDS), a reducing agent (beta-mercaptoethanol), glycerol and bromophenol blue is added, then heated for 5 min at 100° C. before deposition on 15% SDS-PAGE.

E. Purification of Proteins and Complexes.

The resulting bacterial cultures are centrifuged at 4000 rpm for 10 min. The bacterial pellet is suspended in a buffer consisting of 50 mM Tris pH 8.0, 200 mM NaCl, 20 mM imidazole (buffer A) to which is added two pastilles of protease inhibitors, Complete-EDTA free (Roche). The bacterial lysate is carried out by sonication for 4 min then subjected to a centrifugation at 18000 rpm for 20 min in order to recover the soluble fraction containing the Jo and In peptides. This is deposited on a 1 ml HisTrap chromatographic column equilibrated in buffer A, in order to purify the recombinant peptides derived from Jo and In fused to the His6x label. The elution of the individual proteins or in complex is carried out by increasing concentrations of imidazole. The proteins are analyzed on 15% SDS-PAGE. Generally speaking, the recombinant production of derivatives of Jo and In in soluble form in *E. coli*, alone or in complex, has a high yield (between 50 and 100 mg of soluble complex purified per liter of culture) rendering the costs of production minimal and the scaling up practical.

I.2. Results.

A. Formation of the JoIn Complex In Vivo in *E. coli*.

Figure 5:
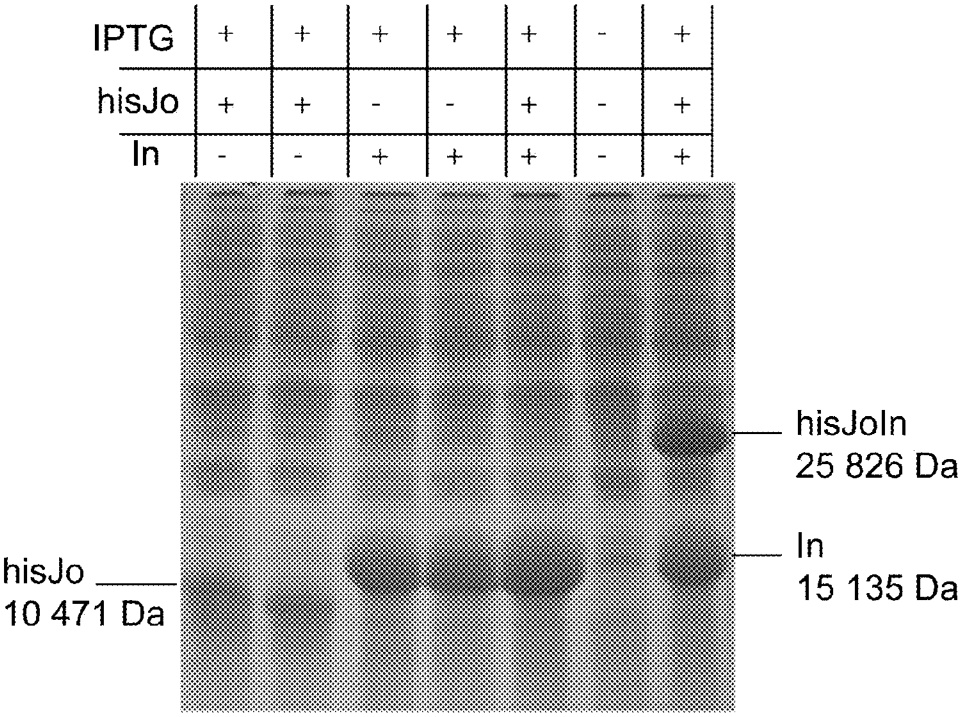
FIG. 5 presents the expression of Jo, In peptides or HisJoIn complex. The molecular masses indicated with regard to recombinant proteins are calculated.

The strains transformed with the vectors pETDuet-HisJo (expression of HisJo), pETDuet-In (expression of In) and pETDuet-HisJoIn (co-expression of HisJo and In) were used. The expression of the derivatives of the Jo or In peptides alone or forming the HisJoIn complex is observed in FIG. 5.

B. Purification of the JoIn Complex.

Figure 6:
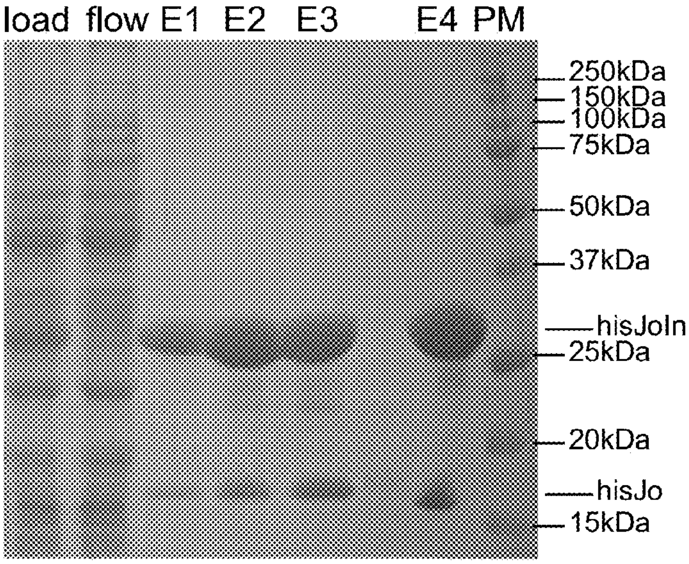
FIG. 6 presents the purification of the HisJoIn complex, wherein PM corresponds to markers of molecular weight and references E1-E4 refer to eluates obtained therefrom.

The HisJoIn complex produced during the co-expression of HisJo and In is purified on HisTrap column (GE Healthcare Life Sciences). The result obtained is presented in FIG. 6.

C. Formation of the JoIn Complex from Purified Jo and In Proteins.

Figure 7:
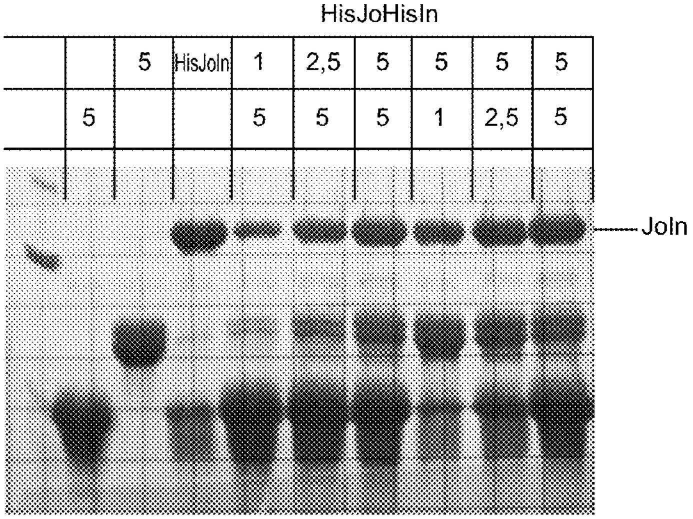
FIG. 7 presents the formation of the HisJoHisIn complex. The volumes of the HisJo and HisIn proteins used are indicated (in µl). The HisJoIn complex is deposited on the gel as control.

The strains transformed with the vectors pETDuet-HisJo (expression of HisJo) and pACYCDuet-HisIn (expression of HisIn) were used. The HisJo and HisIn proteins were purified separately and incubated together, at different ratios as indicated in FIG. 7, for 12 min at ambient temperature before being analyzed on SDS-PAGE.

Complementary kinetic experiments were carried out. Incubation at ambient temperature or at 37° C. does not modify the kinetics of formation of the complex.

D. Purification of the FusJoIn Complex.

Figure 8:
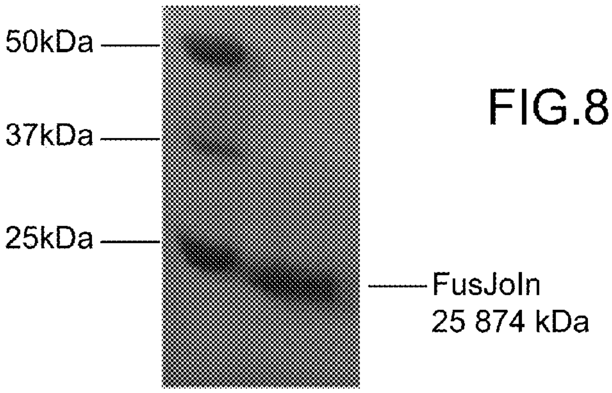
FIG. 8 presents the purification of the FusJoIn complex.

The genes encoding for HisJo and In were fused via a linker encoding for the sequence GSTPGSV. The production and the purification of the FusJoIn complex were carried out according to the previously described protocols (FIG. 8).

II. Characterisation of the JoIn Complex.

II.1. Analysis by Mass Spectrometry in Electrospray Mode.

The purified HisJo and HisIn proteins as well as the purified complexes HisJoIn, HisJoHisIn and FusJoIn were analysed by mass spectrometry in electrospray mode. The formation of the covalent intramolecular bond between Lys191 and Asn695 is accompanied by the loss of an $NH_3$ ion, i.e. a measured mass having lost 17 Da compared to the theoretical mass. All of the experimental data obtained is presented below.

HisJo:

(SEQ ID NO: 9 in the appended listing of sequences)

GSSHHHHHHSQDPSDQYPQTGTYPDVQTPYQIIKVDGSEKNGQHKALNPN

PYERVIPEGTLSKRIYQVNNLDDNQYGIELTVSGKTVYEQKD

| | |
|---|---|
| Mass measured by ESI-MS | 10471 |
| Calculated mass | 10470.32 |

HisIn:

(SEQ ID NO: 10 in the appended listing of sequences)

GSSHHHHHHSQDPTEKKSIENGTITDPMGELIDLQLGTDGRFDPADYTLT

ANDGSRLENGQAVGGPQNDGGLLKNAKVLYDTTEKRIRVTGLYLGTDEKV

TLTYNVRLNDEFVSNKFYDTNGRTTLHPKEVEQNTVRDFPIPKIRD

| | |
|---|---|
| Mass measured by ESI-MS | 16319 |
| Calculated mass | 16317.9 |

HisJoIn:

(SEQ ID NO: 11 in the appended listing of sequences)

GSSHHHHHHSQDPSDQYPQTGTYPDVQTPYQIIKVDGSEKNGQHKALNPN

PYERVIPEGTLSKRIYQVNNLDDNQYGIELTVSGKTVYEQKDADLTEKKS

IENGTITDPMGELIDLQLGTDGRFDPADYTLTANDGSRLENGQAVGGPQN

DGGLLKNAKVLYDTTEKRIRVTGLYLGTDEKVTLTYNVRLNDEFVSNKFY

DTNGRTTLHPKEVEQNTVRDFPIPKIRD

| | |
|---|---|
| Mass measured by ESI-MS | 25589 |
| Calculated mass | 25606.03 |

Formation of the covalent intramolecular bond

HisJoHisIn:

(SEQ ID NO: 12 in the appended listing of sequences)

GSSHHHHHHSQDPSDQYPQTGTYPDVQTPYQIIKVDGSEKNGQHKALNPN

PYERVIPEGTLSKRIYQVNNLDDNQYGIELTVSGKTVYEQKDMGSSHHHH

HHSQDPTEKKSIENGTITDPMGELIDLQLGTDGRFDPADYTLTANDGSRL

ENGQAVGGPQNDGGLLKNAKVLYDTTEKRIRVTGLYLGTDEKVTLTYNVR

LNDEFVSNKFYDTNGRTTLHPKEVEQNTVRDFPIPKIRD

| | |
|---|---|
| Mass measured by ESI-MS | 26772 |
| Calculated mass | 26788.16 |

Formation of the covalent intramolecular bond

FusJoIn:

(SEQ ID NO: 13 in the appended listing of sequences)

GSSHHHHHHSQDPSDQYPQTGTYPDVQTPYQIIKVDGSEKNGQHKALNPN

PYERVIPEGTLSKRIYQVNNLDDNQYGIELTVSGKTVYEQKDGSTPGSVT

EKKSIENGTITDPMGELIDLQLGTDGRFDPADYTLTANDGSRLENGQAVG

-continued

GPQNDGGLLKNAKVLYDTTEKRIRVTGLYLGTDEKVTLTYNVRLNDEFVS

NKFYDTNGRTTLHPKEVEQNTVRDFPIPKIRD

| | |
|---|---|
| Mass measured by ESI-MS | 25857 |
| Calculated mass | 25874 |

Formation of the covalent intramolecular bond

II.2. Mutagenesis of the Residues Involved in the Formation of the Covalent Intramolecular Bond.

Within the scope of the study of the RrgA protein, the residues involved in the formation of the intramolecular bond of the D2 domain between the regions H1 (here named Jo) and H2 (here named In), i.e. Lys191, Asn695 and Asp600 were muted in Ala which led to the abolition of the formation of the covalent bond.

The inventors wished to verify here whether these mutations, borne by the HisJo and HisIn proteins, could also prevent the formation of the isopeptide bond. These mutations were introduced into the constructions encoding for HisJo and HisIn. The native (or wild-type, WT) and mutated proteins were purified then tested in combination for the formation of the complex.

Figure 9:
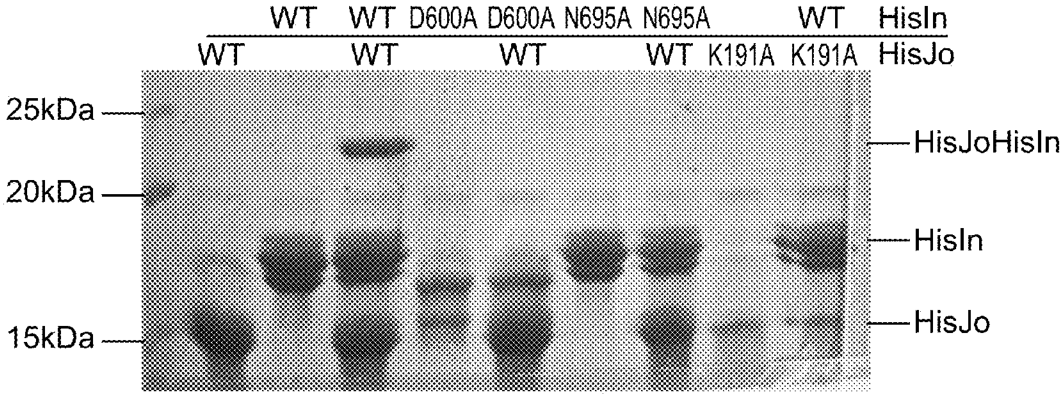
FIG. 9 presents the residues Lys191 and Asn695 forming the covalent bond between Jo and In. The variants of the In peptide migrate in triplet form, the migration of the mutant D600A is altered compared to that of the native protein and mutant N695A. The production rate of the mutant Jo-Lys191 is reduced compared to that of the native Jo form.

The results presented in FIG. 9 show that the formation of the covalent bond between Jo and In is only established with the native forms, indicating that the residues Lys191, Asn695 and Asp600 intervene in the formation of the covalent bond also in in vitro conditions.

II.3. Resolution of the Crystallographic Structure of the HisJoIn Complex.

Figure 10:
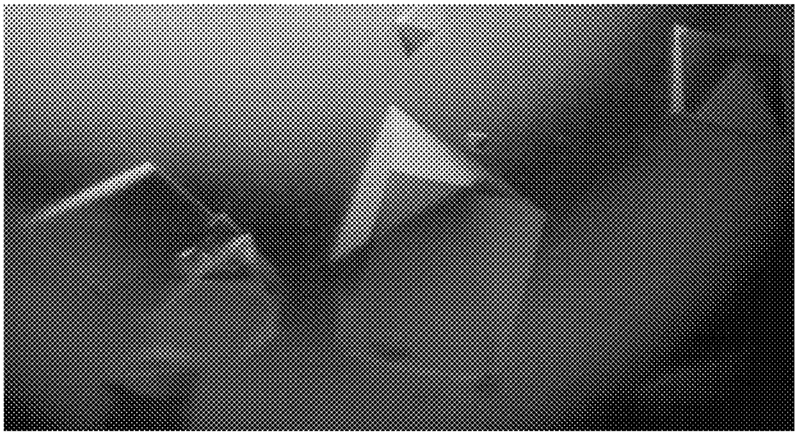
FIG. 10 presents crystals of the HisJoIn complex. The crystallographic structure of the Jo/In complex isolated and reconstituted in vitro has been determined (not shown).

Crystals were obtained by the hanging drop method in the following conditions in 3-4 days:

protein concentration: 23 mg/ml crystallization solution: 1.6 M ammonium sulphate, 0.1 M citric acid, pH 4.0 temperature: 20° C. (FIG. 10).

Diffraction data at 2 Å were collected at ESRF (Grenoble). The resolution of the structure is currently being determined by molecular replacement.

III. Stability of the JoIn Complex.

The covalent bond established spontaneously between the Jo and In peptides stabilizes the JoIn complex.

Figure 11:
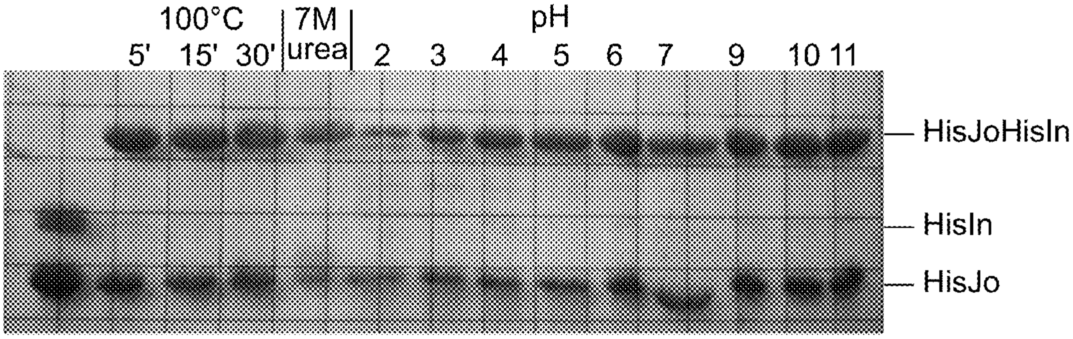
FIG. 11 presents the resistance of the JoIn complex to denaturation by heat, urea and pH variations, with the HisJo and HisIn forms deposited on gel as control.

The inventors have shown that the covalent complex established between the peptides derived from Jo and In is resistant to denaturation by heat, by a chaotropic agent, by variations in pH between 2 and 11, to the action of detergents (not shown). The HisJoHisIn complex was incubated for 30 min or 1 h in the presence of these different agents at ambient temperature before being analysed by SDS-PAGE. The HisJo and HisIn forms are deposited on gel as control (FIG. 11).

The complex formed between the peptides derived from Jo and of In is resistant to proteolytic digestion by trypsin in concentration ratios of 1:1 (gel not shown).

IV. Use of the JoIn Complex in the Engineering of Circular Proteins.

This specific application of the JoIn complex relates to the production of soluble fragments of membrane proteins so as to functional and structural studies and the production of soluble antigens.

IV.1. Context and Objectives.

Soluble regions (in general loops) exposed by membrane proteins can play a functional and/or structural role (for example multimerization).

The fusion of such a loop to the Jo-In covalent complex, thereby mimicking the transmembrane regions, can favour the structuring, the exposure and the production of these regions. In addition, these fusion proteins are soluble, constitute antigens easier to produce and to purify, the antigenicity of which may be increased in comparison with the context of the native membrane protein.

Furthermore, this mode of antigen production has a lower cost in comparison with the synthesis of peptides. The antigen circularized by the addition at the N- and C-termini thereof of Jo and In (or conversely) is expected as being more stable than an isolated peptide.

In addition, the presence of Jo and In in the sequence facilitates the production in abundance of a soluble protein in abundant quantity in *E. coli*. It is also possible that the presence of two fragments of proteins derived from a pathogen bacterium (pneumococci) plays the role of an adjuvant stimulating the production of antibodies.

The example hereafter is an example of application concerning the expression of a loop of 56 amino acids (fragment of protein named BC1K) belonging to a potassium channel (CK) the predicted topology of which includes 4 transmembrane regions.

IV.2. Materials and Methods.

A. Construction of a Vector for the Production of Circular Proteins.

The plasmid derived from pET-Duet-1 (Novagen) containing the nucleotide sequences ( . . . cggttagtgggaaaacagtgtatgaacaaaaagatggttctaccccgggttctgttactgaaaagaaatcaattgagaat ggtacg . . . ) (SEQ ID NO: 14 in the appended sequence listing) encoding for a derivative of Jo (partial sequence in bold) and a derivative of In (partial sequence in italics) separated by a linker of 7 amino acids GSTPGSV (SEQ ID NO: 15 in the appended sequence listing) were modified by directed mutagenesis using the synthetic oligonucleotides Mut 1 and Mut 2 (Table 1) to obtain the expression vector Jo-MCS1-In.

TABLE 1

| | |
|---|---|
| Oligo 1 | 5'CGGTTAGTGGGAAAACAGTGTATGAACAAAAAGATGGAATTCGGTACCCCTGCAGGGAGCTGAAGCTTACTGAAAAGAAATCAATTGAGAATGGTACG (SEQ ID NO: 16 in the appended sequence listing) |
| Oligo 2 | 5'CGTACCATTCTCAATTGATTTCTTTTCAGTAAGCTTCAGCTCCCTGCAGGGGTACCGAATTCCATCTTTTTGTTCATACACTGTTTTCCCACTAACCG( SEQ ID NO: 17 in the appended sequence listing) |
| Oligo 3 | 5'GCGCGAATTCCAGAAATTTCTCAGCGTACG (SEQ ID NO: 18 in the appended sequence listing) |
| Oligo 4 | 5'GCGCAAGCTTGCTGATTTGGTTTGATG (SEQ ID NO: 19 in the appended sequence listing) |

B. Cloning of B1CK in the Jo-MCS1-In Vector.

The sequence encoding for B1CK is amplified by PCR using the Oligos 3 and 4 (Table 1). This fragment of PCR is purified and cloned using the PCR-Script Amp Cloning kit (Agilent). The PCR-Script Amp-B1CK vector is digested simultaneously by the restriction enzymes EcoRI and HindIII to produce a fragment of 167 nucleotides. This fragment purified on agarose gel is then ligated in the Jo-MCS1-In vector pre-cleaved by EcoRI and HindIII and the ligation product is transformed in the *E. coli* strain DH5alpha. The recombinant vector purified from a transformed clone is named Jo-B1CK-In.

C. Expression in *E. Coli* and Purification of B1CK.

The Jo-B1CK-In vector is transformed in the strain BL21 (DE3)Star (Invitrogen). The transformed strain is cultivated in 1 liter of LB culture medium at 37° C. up to an $OD_{600}$ of 0.6 to be then induced by 0.5 mM of IPTG overnight at 20° C. The bacterial culture is centrifuged for 10 min at 5000 g and the bacterial pellet is suspended in 50 mL of 50 mM Tris buffer pH: 7.5, NaCl 150 mM, imidazole 25 mM. The bacteria are lysated by a treatment of 3 cycles in the microfluidizer of 10000 psi. The lysate is centrifuged for 25 min at 40000 g.

The supernatant is loaded on a column of 1 mL of NiNTA (GE Healthcare), washed with 100 mL of 100 mM Tris buffer pH: 7.5, NaCl 150 mM, imidazole 50 mM. The proteins are eluted by an imidazole gradient of 50 mM to 300 mM in 50 mM Tris buffer pH: 7.5, NaCl 150 mM. The fractions containing the absorption peak at 280 nm are combined together and concentrated 20 to 50 times using a Centricon Amicon Ultra 10K (Millipore). The proteins are directly used for the production of antibodies in rabbits (Covalab) after dialysis against a volume of 100 times of 20 mM phosphate buffer 50 mM NaCl pH 7.5.

The analysis of the degree of purity, homogeneity in solution and degree of oligomerization of the fusion protein is carried out by SDS-PAGE in the presence or in the absence of 25 mM dithiothreitol and by gel exclusion chromatography using a S200 10/300GL column (GE Healthcare).

IV.3. Results.

A. Construction of a Vector for the Production of Circular Proteins.

The restriction sites successively in the sequence, EcoRI, KpnI, PstI, SacI and HindIII were inserted by directed mutagenesis between the sequences encoding for Jo and In.

TTTTGTTTAACTTTAAGAAGGAGATATACCATGGGCAGCAGC*CATCA*

*CCATCATCAC*CACAGCCAGGATCCGTCTGACCAGTATCCACAAACAG

GGACTTATCCAGATGTTCAAACACCTTATCAGATTATTAAGGTAGAT

GGTTCGGAAAAAAACGGACAGCACAAGGCGTTGAATCCGAATCCATA

TGAACGTGTGATTCCAGAAGGTACACTTTCAAAGAGAATTTATCAAG

TGAATAATTTGGATGATAACCAATATGGAATCGAATTGACGGTTAGT

GGGAAAACAGTGTATGAACAAAAAGATGGAATTCGGTACCCCTGCAG

GGAGCTGAAGCTT*ACTGAAAAGAAATCAATTGAGAATGGTACGATTA*

*CAGATCCGATGGGTGAGTTAATTGATTTGCAATTGGGCACAGATGGA*

*AGATTTGATCCAGCAGATTACACTTTAACTGCAAACGATGGTAGTCG*

*CTTGGAGAATGGACAAGCTGTAGGTGGTCCACAAAATGATGGTGGTT*

*TGTTAAAAAATGCAAAAGTGCTCTATGATACGACTGAGAAAAGGATT*

*CGTGTAACAGGTCTGTACCTTGGAACGGATGAAAAAGTTACGTTGAC*

*CTACAATGTTCGTTTGAATGATGAGTTTGTAAGCAATAAATTTTATG*

*ATACCAATGGTCGAACAACCTTACATCCTAAGGAAGTAGAACAGAAC*

*ACAGTGCGCGACTTCCCGATTCCTAAGATTCGTGATTGA*CTCGAGTC

TGGT . . .

The above sequence (SEQ ID NO: 20 in the appended sequence listing) corresponds to the nucleotide sequence of the relevant region of the cloning vector enabling the expression of a fusion protein having the Jo and In proteins localized respectively in N and C-terminus of the protein. In underlined italics: nucleotide sequence encoding for 6 histidines; in bold: nucleotide sequence encoding for a derivative of Jo; in italics: nucleotide sequence encoding for a derivative of In; and between the nucleotide sequence encoding for the derivative of Jo and that encoding for the derivative of In, the multiple cloning site (5 restriction sites underlined). The expression of the fusion protein is under the control of the promoter T7Lac.

B. Cloning of Loop 1 of CK (B1CK) in the "Jo-In" Vector.

The sequence encoding for the B1CK loop was inserted between the sequences Jo and In.

ATGGGCAGCAGC*CATCACCATCATCACCAC*AGCCAGGATCCGTCTG

ACCAGTATCCACAAACAGGGACTTATCCAGATGTTCAAACACCTTA

TCAGATTATTAAGGTAGATGGTTCGGAAAAAAACGGACAGCACAAG

GCGTTGAATCCGAATCCATATGAACGTGTGATTCCAGAAGGTACAC

TTTCAAAGAGAATTTATCAAGTGAATAATTTGGATGATAACCAATA

TGGAATCGAATTGACGGTTAGTGGGAAAACAGTGTATGAACAAAAA

GATGGAATTCCAGAAATTTCTCAGCGTACGACCATTGTGATTCAGA

AACAAACGTTTATCAGTCAGCATTCCTGTGTGAATAGCACCGAACT

GGATGAACTGATCCAACAAATTGTGGCAGCGATCAATGCCGGTATT

ATTCCACTGGGGAACACATCAAACCAAATCAGCAAGCTT*ACTGAAA*

*AGAAATCAATTGAGAATGGTACGATTACAGATCCGATGGGTGAGTT*

*AATTGATTTGCAATTGGGCACAGATGGAAGATTTGATCCAGCAGAT*

*TACACTTTAACTGCAAACGATGGTAGTCGCTTGGAGAATGGACAAG*

*CTGTAGGTGGTCCACAAAATGATGGTGGTTTGTTAAAAAATGCAAA*

*AGTGCTCTATGATACGACTGAGAAAAGGATTCGTGTAACAGGTCTG*

*TACCTTGGAACGGATGAAAAAGTTACGTTGACCTACAATGTTCGTT*

*TGAATGATGAGTTTGTAAGCAATAAATTTTATGATACCAATGGTCG*

*AACAACCTTACATCCTAAGGAAGTAGAACAGAACACAGTGCGCGAC*

*TTCCCGATTCCTAAGATTCGTGATTGA*CTCGAGTCTGGT

The above sequence (SEQ ID NO: 21 in the appended sequence listing) corresponds to the nucleotide sequence of the relevant region of the vector enabling the expression of a fusion protein having the Jo and In proteins localized respectively in N and C-terminus of loop 1 of the potassium channel. In underlined italics: nucleotide sequence encoding for 6 histidines; in bold: nucleotide sequence encoding for a derivative of Jo; in italics: nucleotide sequence encoding for a derivative of In; and, between the nucleotide sequence encoding for the derivative of Jo and that encoding for the derivative of In, in underlined, nucleotide sequence encoding for loop 1 of the potassium channel and, in non-underlined, nucleotide sequences encoding for the amino acids of the linker.

MGSS*HHHHHH*SQDPSDQYPQTGTYPDVQTPYQIIKVDGSEKNGQ

HKALNPNPYERVIPEGTLSKRIYQVNNLDDNQYGIELTVSGKTV

YEQKDGIPEISQRTTIVIQKQTFISQHSCVNSTLDELIQQIVAA

INAGIIPLGNTSNQISKL*TEKKSIENGTITDPMGELIDLQLGTD*

-continued

*GRFDPADYTLTANDGSRLENGQAVGGPQNDGGLLKNAKVLYDTT*

*EKRIRVTGLYLGTDEKVTLTYNVRLNDEFVSNKFYDTNGRTTLH*

*PKEVEQNTVRDFPIPKIRD* Stop

The above sequence (SEQ ID NO: 22 in the appended sequence listing) corresponds to the amino acid sequence of the fusion Jo-B1CK-In. In underlined italics: sequence of the label of 6 histidines; in bold: amino acid sequence of the derivative of Jo; in italics: amino acid sequence of the derivative of In; and, between the amino acid sequence of the derivative of Jo and that encoding for the derivative of In, underlined amino acid sequence of loop 1 of the potassium channel and non-underlined amino acid sequence of the linker. Total number of residues: 284, calculated molecular mass: 31 677.1 Da.

C. Purification of the Jo-B1CK-In Protein and Analysis in the Presence and in the Absence of a Reducing Agent.

The recombinant protein Jo-B1CK-In purified by affinity on NiNTA column is analyzed by SDS-PAGE in the presence or not of a reducing agent, DTT.

Figure 12:
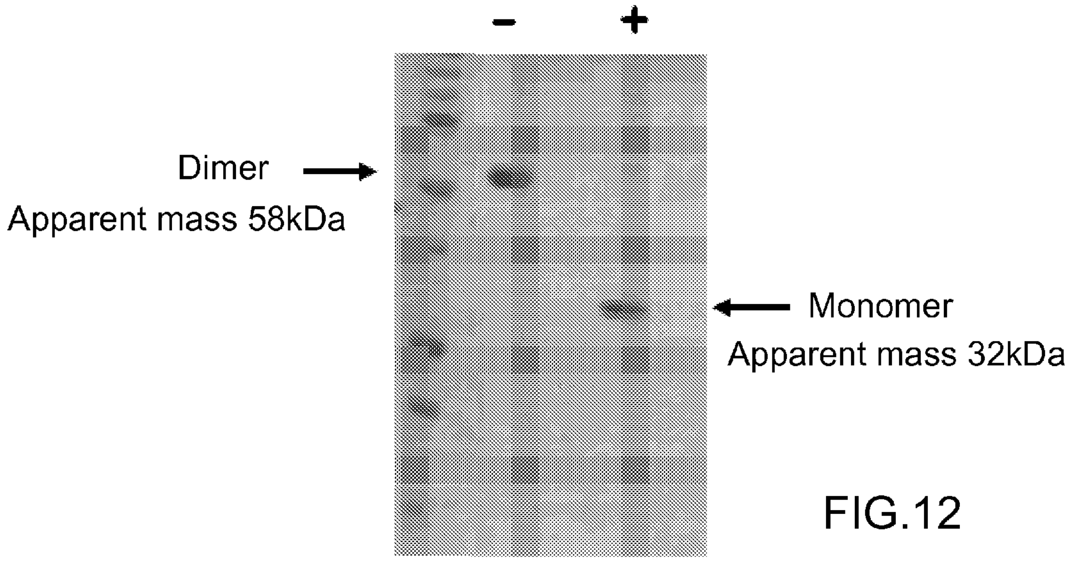
FIG. 12 presents an electrophoresis gel of the Jo-B1CK-In protein purified by affinity chromatography on NiNTA column and analysed by SDS-PAGE in the absence (−) and in the presence (+) of 25 mM of DTT.

In the presence of DTT, the protein migrates with an apparent mass of 32 kDa against a double mass in the absence of the reducing agent (FIG. 12). Recent publications describing high resolution structures of homologous proteins indicating that said channels dimerize by a disulphide bridge localized on a loop, which corresponds to the B1CK loop which contains a cysteine (Miller & Long, 2012, Science, vol. 335, pages 432-436; Brohawn et al., 2012, Science, vol. 335, pages 436-441).

The dimerization by the cysteines of Jo-B1CK-In demonstrates that loop 1 of the channel K constrained at the base thereof by the Jo-In protein has a native configuration. Consequently, the Jo-In platform mimics the effect of the two transmembrane regions bearing the loop 1.

Figure 13:
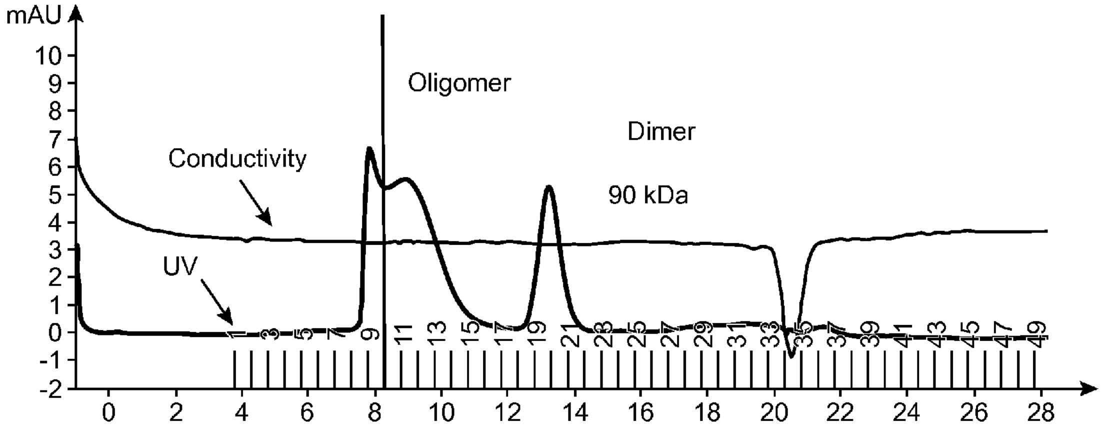
FIG. 13 shows that the apparent molecular mass of the peak between the fractions 19 and 21 corresponds to that of a globular protein used for the calibration of the column (Filtration on gel).

These results were confirmed by gel filtration. The protein is eluted as a globular protein of 90 kDa corresponding to the dimer (theoretical mass 63 kDa). No trace of monomer is detected. The dimerization is not due to the interaction between two covalent Jo-In complexes because a Jo-In fused via a linker of 7 amino acids instead to the loop 1, migrates in monomeric form in identical experimental conditions (data not presented). The fact that the Jo-B1CK-In dimer migrates through the column with an apparent mass (90 kDa) greater than the theoretical mass (63 kDa) could stem from the mobility in solution of the loop. The species of higher apparent molecular mass (multimers) probably stems from bonding between Jo and In belonging to independent molecules (circular Jo-B1CK-In-Jo-B1CK-In, the Jo and In at the ends being covalently bonded)) bound together by the cysteines of loop 1 (FIG. 13).

D. Production of Antibodies in Rabbits.

The purified Jo-B1CK-In protein was used to produce polyclonal antibodies in rabbits (supplier Covalab).

Figure 14:
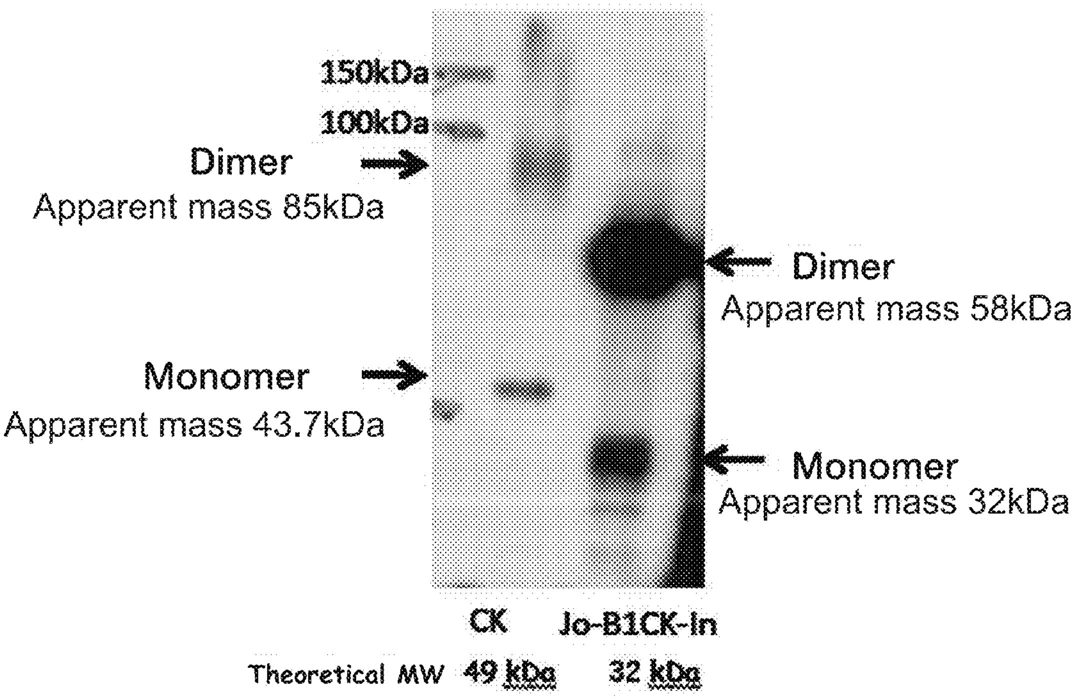

The sera collected 53 days after injection were tested for their capacity to detect Jo-B1CK-In and the recombinant K channel (CK) (FIG. 14). The sera diluted 10,000 times efficiently recognize the two proteins. The Jo-In platform is thus effective for the production of polyclonal antibodies against membrane proteins which are often difficult to produce and which have reduced antigenic properties.

The invention claimed is:

1. A heterodimer formed by two peptides bound to each other by an isopeptide bond, wherein one of the two peptides is selected from the group consisting of the Jo peptide of SEQ ID NO: 2, a derivative of the Jo peptide of SEQ ID NO: 2 and a fragment of the Jo peptide of SEQ ID NO: 2 and the other peptide is selected from the group consisting of the In peptide of SEQ ID NO: 4, a derivative of the In peptide of SEQ ID NO: 4 and a fragment of the In peptide of SEQ ID NO: 4.

2. A solid support on the surface of which one (or more) peptide(s) is(are) immobilized, wherein the peptide(s) are selected from the group consisting of the Jo peptide of SEQ ID NO: 2, a derivative of the Jo peptide of SEQ ID NO: 2, a fragment of the Jo peptide of SEQ ID NO: 2, the In peptide of SEQ ID NO: 4, a derivative of the In peptide of SEQ ID NO: 4 and a fragment of the In peptide of SEQ ID NO: 4.

3. A compound conjugated with at least one peptide selected from the group consisting of the Jo peptide of SEQ ID NO: 2, a derivative of the Jo peptide of SEQ ID NO: 2, a fragment of the Jo peptide of SEQ ID NO: 2, the In peptide of SEQ ID NO: 4, a derivative of the In peptide of SEQ ID NO: 4 and a fragment of the In peptide of SEQ ID NO: 4.

4. The compound according to claim 3, wherein said compound is a biological or biologically active molecule, a monomer, an easily detectable compound or a cytotoxic compound.

5. The compound according to claim 4, wherein said compound is conjugated with two peptides, identical or different, each selected from the group consisting of the Jo peptide of SEQ ID NO: 2, a derivative of the Jo peptide of SEQ ID NO: 2, a fragment of the Jo peptide of SEQ ID NO: 2, the In peptide of SEQ ID NO: 4, a derivative of the In peptide of SEQ ID NO: 4 and a fragment of the In peptide of SEQ ID NO: 4.

6. A method for purifying a compound, comprising:

conjugating indirectly said compound with one of the peptides selected from either group (a) consisting of the Jo peptide of SEQ ID NO: 2, a derivative of the Jo peptide of SEQ ID NO: 2 and a fragment of the Jo peptide of SEQ ID NO: 2 or from group (b) consisting of the In peptide of SEQ ID NO: 4, a derivative of the In peptide of SEQ ID NO: 4 and a fragment of the In peptide of SEQ ID NO: 4, to form a conjugated compound, a cleavable spacer arm separating said compound and said peptide;

preparing a solid support on the surface of which a peptide from the other of group (a) or group (b) is immobilized;

placing the conjugated compound in the presence of the solid support whereby the conjugated compound is immobilized on the solid support;

subjecting the conjugated compound thereby immobilized to conditions enabling the cleavage thereof; and recovering the purified cleaved compound.

7. A biochip or biosensor prepared using a solid support having on the surface thereof one (or more) peptide(s) selected from either group (a) consisting of the Jo peptide of SEQ ID NO: 2, a derivative of the Jo peptide of SEQ ID NO: 2 and a fragment of the Jo peptide of SEQ ID NO: 2 or from group (b) consisting of the In peptide of SEQ ID NO: 4, a derivative of the In peptide of SEQ ID NO: 4 and a fragment of the In peptide of SEQ ID NO: 4; and a compound conjugated with at least one peptide from the other of group (a) or group (b), said derivatives and fragments being capable of forming a covalent complex.

8. A medical or diagnostics composition comprising the compound according to claim 4, wherein said compound is a biological or biologically active molecule, an easily detectable compound or a cytotoxic compound.

9. A diagnostic or treatment kit comprising:

in a $1^{st}$ compartment, a $1^{st}$ compound according to claim 3 capable of recognizing or targeting a pathologic site and conjugated with one of the peptides selected from either group (a) consisting of the Jo peptide of SEQ ID NO: 2, a derivative of the Jo peptide of SEQ ID NO: 2 and a fragment of the Jo peptide of SEQ ID NO: 2 or from group (b) consisting of the In peptide of SEQ ID NO: 4, a derivative of the In peptide of SEQ ID NO: 4 and a fragment of the In peptide of SEQ ID NO: 4; and in a $2^{nd}$ compartment, a $2^{nd}$ easily detectable or cytotoxic compound bound to a peptide from the other of group (a) or group (b).

10. A method for crystallizing a compound according to claim 3, comprising:

conjugating said compound with one of the peptides selected from either group (a) consisting of the Jo peptide of SEQ ID NO: 2, a derivative of the Jo peptide of SEQ ID NO: 2 and a fragment of the Jo peptide of SEQ ID NO: 2 or from group (b) consisting of the In peptide of SEQ ID NO: 4, a derivative of the In peptide of SEQ ID NO: 4 and a fragment of the In peptide of SEQ ID NO: 4, to form a conjugated compound;

placing the conjugated compound in the presence of a peptide from the other of group (a) or group (b) to obtain a conjugated product; and subjecting the conjugated product thereby obtained to conditions enabling the crystallization thereof.

11. A circular structure comprising at least one compound as defined in claim 4.

12. A multimeric structure comprising at least two compounds as defined in claim 4 and, optionally, a plurality of compounds as defined in claim 4, identical or different, each compound being bound to at least one other compound by an isopeptide bond.

13. A circular structure comprising at least one compound as defined in claim 5.

14. A multimeric structure comprising at least two compounds as defined in claim 5 and, optionally, a plurality of compounds as defined in claim 5, identical or different, each compound being bound to at least one other compound by an isopeptide bond.

* * * * *